(12) United States Patent
Noronha et al.

(10) Patent No.: US 6,927,246 B2
(45) Date of Patent: Aug. 9, 2005

(54) POLYMERS FUNCTIONALIZED WITH FLUORESCENT BORONATE MOTIFS AND METHODS FOR MAKING THEM

(75) Inventors: Glenn Noronha, Oceanside, CA (US); Jonathan Reilly, Reseda, CA (US); Joseph C. Walsh, Los Angeles, CA (US); Brooks Cochran, Northridge, CA (US); Aaron M. Heiss, Orange, OH (US); Bill C. Ponder, Fort Worth, TX (US); David J. Vachon, Granada Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 501 days.

(21) Appl. No.: 10/075,415

(22) Filed: Feb. 14, 2002

(65) Prior Publication Data

US 2002/0197724 A1 Dec. 26, 2002

Related U.S. Application Data

(60) Provisional application No. 60/269,226, filed on Feb. 15, 2001.

(51) Int. Cl.[7] .................................................. C08K 5/55
(52) U.S. Cl. .......................... 524/184; 525/259; 436/95
(58) Field of Search ..................... 524/184; 525/259; 436/95

(56) References Cited

U.S. PATENT DOCUMENTS

| | | |
|---|---|---|
| 4,236,071 A | 11/1980 | Chimenti |
| 4,401,122 A | 8/1983 | Clark, Jr. |
| 4,428,366 A | 1/1984 | Findl et al. |
| 4,455,741 A | 6/1984 | Kolodner |
| 4,496,722 A | 1/1985 | Gallop et al. |
| 4,542,987 A | 9/1985 | Hirschfeld |
| 4,600,306 A | 7/1986 | Hara et al. |

(Continued)

FOREIGN PATENT DOCUMENTS

| | | |
|---|---|---|
| EP | 0 673 622 A3 | 9/1995 |
| EP | 0 693 271 A1 | 1/1996 |
| EP | 0729 962 A1 | 9/1996 |
| FR | 2 253 794 | 7/1975 |
| GB | 2 284 809 | 6/1995 |
| WO | WO 82/01804 | 5/1982 |
| WO | WO 91/04488 | 4/1991 |
| WO | WO 91/18912 | 12/1991 |
| WO | WO 96/03074 | 2/1996 |
| WO | WO 97/19188 | 5/1997 |
| WO | WO 97/29154 | 8/1997 |
| WO | WO 98/22820 | 5/1998 |
| WO | WO 99/46600 | 9/1999 |
| WO | WO 01/18543 | 3/2001 |
| WO | WO 01/20334 | 3/2001 |
| WO | WO 02/054067 | 7/2002 |

OTHER PUBLICATIONS

Appleton et al., "Detection of Total Sugar Concentration Using Photoinduced Electron Transfer Materials: Development of Operationally Stable, Reusable Optical Sensors," Sensors and Actuators B, Elsevier Sequoia, 2000, 65(1–3): 302–304.

Arnold et al., "Determination of Physiological Levels . . . Spectra," Anal. Chem., 1990, 62:1457–1464.

(Continued)

*Primary Examiner*—William K. Cheung
(74) *Attorney, Agent, or Firm*—Gates & Cooper LLP

(57) ABSTRACT

Improved polymer matrices which incorporate fluorescent biosensor molecules as well as methods of making and using these polymer matrices are described. Such matrices can be used in fluorescent biosensors and biosensor systems, including those which are used in the detection of polyhydroxylated analytes such as glucose. The properties of the polymer matrices of the invention renders biosensors utilizing such matrices particularly well-suited for detecting and measuring in-vivo glucose concentrations.

26 Claims, 34 Drawing Sheets

U.S. PATENT DOCUMENTS

| | | |
|---|---|---|
| 4,655,225 A | 4/1987 | Dahne et al. |
| 4,680,268 A | 7/1987 | Clark, Jr. |
| 4,805,623 A | 2/1989 | Jobsis |
| 4,861,728 A | 8/1989 | Wagner |
| 4,875,486 A | 10/1989 | Rapoport et al. |
| 4,882,492 A | 11/1989 | Schlager |
| 4,923,819 A | 5/1990 | Fernandez et al. |
| 4,924,009 A | 5/1990 | Neckers et al. |
| 4,929,387 A | 5/1990 | Hayden et al. |
| 4,974,929 A | 12/1990 | Curry |
| 5,028,787 A | 7/1991 | Rosenthal et al. |
| 5,032,315 A | 7/1991 | Hayden et al. |
| 5,049,738 A | 9/1991 | Gergely et al. |
| 5,054,487 A | 10/1991 | Clarke |
| 5,070,874 A | 12/1991 | Barnes et al. |
| 5,077,476 A | 12/1991 | Rosenthal |
| 5,086,229 A | 2/1992 | Rosenthal et al. |
| 5,101,814 A | 4/1992 | Palti |
| 5,112,124 A | 5/1992 | Harjunmaa et al. |
| 5,137,833 A | 8/1992 | Russell |
| 5,173,456 A | 12/1992 | Hayden et al. |
| 5,182,214 A | 1/1993 | Kessler et al. |
| 5,196,709 A | 3/1993 | Berndt et al. |
| 5,198,670 A | 3/1993 | VanCauter et al. |
| 5,203,328 A | 4/1993 | Samuels et al. |
| 5,235,045 A | 8/1993 | Lewis et al. |
| 5,235,606 A | 8/1993 | Mourou et al. |
| 5,246,867 A | 9/1993 | Lakowicz et al. |
| 5,262,526 A | 11/1993 | Sasamoto et al. |
| 5,270,548 A | 12/1993 | Steinkamp |
| 5,279,543 A | 1/1994 | Glikfeld et al. |
| 5,281,825 A | 1/1994 | Berndt et al. |
| 5,308,773 A | 5/1994 | Lewis et al. |
| 5,313,485 A | 5/1994 | Hamil et al. |
| 5,322,796 A | 6/1994 | Ishikawa |
| 5,342,789 A | 8/1994 | Chick et al. |
| 5,353,790 A | 10/1994 | Jacques et al. |
| 5,362,307 A | 11/1994 | Guy et al. |
| 5,409,835 A | 4/1995 | Lakowicz et al. |
| 5,439,797 A | 8/1995 | Tsien et al. |
| 5,445,611 A | 8/1995 | Eppstein et al. |
| 5,458,140 A | 10/1995 | Eppstein et al. |
| 5,476,094 A | 12/1995 | Allen et al. |
| 5,485,530 A | 1/1996 | Lakowicz et al. |
| 5,495,850 A | 3/1996 | Zuckerman |
| 5,503,770 A | 4/1996 | James et al. |
| 5,504,337 A | 4/1996 | Lakowicz et al. |
| 5,512,246 A | 4/1996 | Russell et al. |
| 5,515,864 A | 5/1996 | Zuckerman |
| 5,528,046 A | 6/1996 | Ishikawa |
| 5,528,611 A | 6/1996 | Scheps |
| 5,590,141 A | 12/1996 | Baird et al. |
| 5,599,504 A | 2/1997 | Hosoi et al. |
| 5,626,134 A | 5/1997 | Zuckerman |
| 5,628,310 A | 5/1997 | Rao et al. |
| 5,648,270 A | 7/1997 | Kuhn et al. |
| 5,666,373 A | 9/1997 | Sharp et al. |
| 5,674,743 A | 10/1997 | Ulmer |
| 5,763,238 A | 6/1998 | James et al. |
| 5,776,782 A | 7/1998 | Tsuji |
| 5,784,157 A | 7/1998 | Gorfinkel et al. |
| 5,798,306 A | 8/1998 | Dickinson, Jr. |
| 5,814,820 A | 9/1998 | Dong et al. |
| 5,818,582 A | 10/1998 | Fernandez et al. |
| 5,825,798 A | 10/1998 | Momiuchi et al. |
| 5,846,726 A | 12/1998 | Nadeau et al. |
| 5,865,754 A | 2/1999 | Sevick-Muraca et al. |
| 5,888,739 A | 3/1999 | Pitner et al. |
| 5,909,278 A | 6/1999 | Deka et al. |
| 5,911,952 A | 6/1999 | Tsuji |
| 5,919,630 A | 7/1999 | Nadeau et al. |
| 5,928,869 A | 7/1999 | Nadeau et al. |
| 5,935,791 A | 8/1999 | Nadeau et al. |
| 5,952,236 A | 9/1999 | Thompson et al. |
| 5,955,737 A | 9/1999 | Hallidy et al. |
| 5,981,957 A | 11/1999 | Cruce et al. |
| 5,987,049 A | 11/1999 | Weingarten et al. |
| 5,990,484 A | 11/1999 | Ohsuka |
| 5,994,707 A | 11/1999 | Mendoza et al. |
| 6,002,954 A * | 12/1999 | Van Antwerp et al. ..... 600/317 |
| 6,011,984 A | 1/2000 | Van Antwerp et al. |
| 6,040,194 A | 3/2000 | Chick et al. |
| 6,157,037 A | 12/2000 | Danielson |
| 6,184,535 B1 | 2/2001 | Kashima et al. |
| 6,200,818 B1 | 3/2001 | Eigen et al. |
| 6,214,628 B1 | 4/2001 | Lakowicz et al. |
| 6,225,127 B1 | 5/2001 | Thompson et al. |
| 6,344,360 B1 | 2/2002 | Colvin et al. |

OTHER PUBLICATIONS

Bostick et al., "Quantitative Determination of Blood . . . Luminol," Anal. Chemistry, 1975, 47(3):447–452.

Burnett et al., "Synthesis of a Fluorescent Boronic Acid . . . Erythrocytes," Biochemical and Biophysical Research Communications, 1980, 96(1): 157–162.

Czarnik, "Chemical Communication in . . . Chemosensors," Acc. Chem. Res., 1994, 27:302–308.

DCCT Research Group, "The Effect of Intensive Treatment . . . Mellitus," The New England Journal of Medicine, 1993, 329(14):977–986.

Falasca et al., "Purification and Partial . . . Sativa," Biochimica et Biophysica Acta, 1979, 577:71–81.

Gough et al., "Development of the Implantable Glucose Sensor," Diabetes, 1995, 44:1005–1009.

Guilbault et al., "Homovanillic Acid as a . . . Enzymes," Analytic Chemistry, 1968, 40(1):190–196.

Indelli et al., "Salt Effects in the Reaction . . . Ions," Journal of the American Chemical Society, 1960, 82(13):3233, 3863–3866.

James et al., "Novel Photoinduced . . . Amine," J. Chem. Soc., Chem. Commun., 1994, pp. 477–478.

James, et al., "Novel Saccharide–Photoinduced . . . Amine," J. Am. Chem. Soc., 1995, 117:8982–8987.

James et al., "Chiral discrimination of . . . sensor," Nature, 1995, 374:345–347.

Joon et al., "Fluorescent chemosensors . . . found," SPIE, 1992, vol. 1796, pp. 87–91.

Lakowicz, et al., "Emerging Biomedical and Advanced Applications . . . Spectroscopy," Journal of Fluorescence, 1994, 4(1):117–136.

Lakowicz et al., "Fluorescence lifetime–based sensing . . . glucose," Sensors and Actuators B, 1993, 11:133–143.

Lin et al., J. Org. Chem., 1979, 44(25):4701–4703.

Kemp et al., "Synthesis of Cyclophanes . . . methylnaphthalenes," The Journal of Organic Chemistry, 1979, 44(25):4700–4703.

Marquardt et al., "Near–Infrared Spectroscopic . . . Matrix," Anal. Chem., 1993, 65:3271–3278.

Mohler et al., "α–Amino Acid Chelative . . . Acid," J. Am. Chem. Soc., 1993, 115:7037–7038.

Monroe, "Novel implantable glucose sensors," ACL, 1989, pp. 8–16.

Nakashima et al., "Sugar–Assisted Chirality . . . Complexes," Chemistry Letters, 1994, pp. 1267–1270.

Okafor, "Synthesis, Properties and Uses of Angular Phenoxazines," *Dyes and Pigments,* Elsevier Applied Science Publishers Ltd., England, vol. 7, No. 2, 1986, pp. 103–131, XP-002122264.

Patterson et al., "Tuning the Affinity of a Synthetic Sialic Acid Receptor Using Combinatorial Chemistry," Tetrahedron Lett., 1998, 39(20): 3111–3114.

Pilosof et al., "Microporous Membrane Flow . . . Glucose," Anal. Chem., 1982, 54:1698–1701.

Reach et al., Anal. Chem., 1992, 64(6):381–386.

Sandanayake et al., "Molecular Fluorescence Sensor . . . Coumarin," Chemistry Letters, 1995, pp. 139–140.

Uziel et al., "Direct Labeling of DNA . . . Group," Biochemical and Biophysical Research Communications, 1991, 180(3):1233–1240.

Xuhong, Qian et al., "The Synthesis, Application and Prediction of Stokes Shift in Fluorescent Dyes Derived from 1,8–Naphthalic Anhydride," *Dyes and Pigments,* Elsevier Applied Science Publishers Ltd., England, vol. 11, No. 1, 1989, pp. 13–20, XP–000026521.

Yoon et al., "Fluorescent chemosensors . . . found[1]," SPIE, 1992, 1796:87–91.

Yoon et al., "Fluorescent Chemosensors of . . . Quenching[1]," J. Am. Chem. Soc. 1992, 114:5874–5875.

* cited by examiner

NH$_2$-FBA

NH$_2$-FBA

NH$_2$-FBA

NH2-FBA

SO₃H-FBA

POLYMERS FUNCTIONALIZED WITH FLUORESCENT BORONATE MOTIFS AND METHODS FOR MAKING THEM

RELATED APPLICATIONS

This application claims priority under Section 119(e) from U.S. Provisional Application Ser. No. 60/269,226, filed Feb. 15, 2001; and this application is related to U.S. patent application Ser. No. 08/721,262, filed Sep. 26, 1996, now U.S. Pat. No. 5,777,060 which is a Continuation-in-Part of U.S. patent application Ser. No. 08/410,775, filed Mar. 27, 1995, now abandoned; and this application is related to U.S. patent application Ser. No. 09/934,390, filed Aug. 21, 2001, which is a Divisional application of U.S. patent application Ser. No. 09/401,147, filed Sep. 22, 1999 which is a Continuation Application of U.S. patent application Ser. No. 08/752,945, filed Nov. 21, 1996, now U.S. Pat. No. 6,011,984, which is a Continuation-in-Part of U.S. Provisional Application Ser. No. 60/007,515; and this application is related to U.S. patent application Ser. No. 10/033,240, filed Dec. 28, 2001; and this application is related to U.S. patent application Ser. No. 09/823,522, filed Mar. 30, 2001, which claims priority to provisional application No. 60/194,673, filed Apr. 4, 2000, and is a Continuation-in-part Application of U.S. patent application Ser. No. 09/663,567, filed Sep. 15, 2000, which claims priority to provisional application No. 60/154,103, filed Sep. 15, 1999; the disclosures of each of which are incorporated herein by reference.

FIELD OF THE INVENTION

The invention is in the field of biological sensors. Specific embodiments of the invention include polymers functionalized with fluorescent boronate motifs for use in biological sensors capable of detecting polyhydroxylated compounds such as glucose.

BACKGROUND OF THE INVENTION

A variety of biological sensors which utilize fluorescence in the detection of molecules are known in the art. Sensors in which molecular recognition coupled with fluorescent quenching for example, are used for the detection of analyte concentrations in a variety of bioassays. In addition to their in vitro applications, the use of biosensors in in vivo is of particular interest to the medical community due to their potential in the amelioration a variety of disease conditions. For example, the concept of implantable biological sensors which can continuously measure glucose levels in diabetic individuals has existed for several decades. A primary goal in this art has been to overcome the disadvantages of capillary blood glucose self-monitoring by developing a glucose sensor, which can provide more frequent and easily acquired glucose information. In addition, an ideal sensor can function as a hypoglycemic and hyperglycemic alarm, and ultimately serve as the controller for an artificial endocrine pancreas. In this context, non-invasive glucose sensors are of particular interest to medical practitioners, and typical approaches to non-invasive blood glucose measurement are described in U.S. Pat. Nos. 4,428,366, 4,655,225, 4,805,623, 4,875,486, 4,882,492, 5,028,787, 5,054,487, 5,070,874, 5,077,476, 5,086,229, and 5,112,124, the disclosures of each being incorporated herein by reference.

The continuous, long-term, real-time ambulatory measurement of glucose concentrations in vivo is an important problem that remains to be solved. The in vitro equivalent is the ability to sense glucose continuously under aqueous physiologically relevant conditions, a challenging enough proposition due to restrictions placed on pH, buffer and temperature. The long-term, continuous glucose measurement problem is of particular significance in diabetes, where such measurement is of crucial importance to ensure proper glycemic control in insulin dependent individuals, and to determine glucose levels for any reason even in non-insulin dependent diabetics. Such measurement in vivo, if capable of being performed in a minimally invasive or non-invasive fashion, would be of tremendous significance, and contribute greatly to the lives of at least 16 million afflicted people in the U.S. alone.

Measurements of glucose might be performed by direct spectroscopic signatures of the glucose molecule, or via the aid of chemical or biological receptors for the glucose molecule, wherein a binding or a binding related event is coupled to a signal transducing method so as to be read either by spectroscopic, amperometric or related means. With a suitable calibration method, such data would enable a continuous glucose measurement. Of the chemical receptors, one of particular note is any boronate containing species since boronates reversibly bind polyols, glucose being one good example of such species. James et. al. describe a phenylboronic acid moiety coupled with a fluorescent molecular component as organic compounds that act as chemical biosensors for polyhydroxylated molecules (see, e.g. James, T. D., et. al., J. Chem. Soc. Chem. Commun., 1994, 477–478). The sensing capabilities of these molecules are determined by the changes (increases or decreases) in fluorescence intensity exhibited upon binding of a polyhydroxylated saccharide, of which glucose is of particular interest. The binding event may be recorded by any proximal reporter species that is capable of sensing and signaling this binding. Colorimetric methods, in which a change is induced by direct or indirect chemical or physical commerce between the boronate and the actual portion reporting the change is fairly common. Fluorescence reporters are of particular value because of the low levels of analyte capable of being sensed, the low amounts of fluorophore required, the inherent sensitivity of fluorescence, and the two or three well-established methods of detecting fluorescence phenomena.

When combined with existing insulin pump technologies, a minimally-invasive, continuous glucose sensor is of great benefit to patients in achieving tighter blood-glucose control. The incorporation of phenylboronic fluorescent compounds in a sensor designed to detect glucose is described in U.S. Pat. No. 6,002,954 to Van Antwerp et al., which discloses an implantable optical sensor designed to facilitate the management of diabetes. In this sensor system, a fluorescent transducer is implanted 1–3 mm below the surface of the skin and optically interrogated externally to determine the level of tissue glucose in diabetic patients.

A number of biological sensors known in the art utilize functional moieties incorporated into macromolecular matrices (e.g. polymers). In this context, the use of such matrices in biological sensors can provide a number of advantages in sensor design, manufacture and use including ease in manipulation. While molecular glucose sensing species have been synthesized and tested, there is a need for in vivo sensors which incorporate these species. In addition, while certain polymer-based sensors are known in the art, there is a need for improved macromolecular matrices which can attach glucose sensing species in an active sensor and methods for making such matrices. Specifically, there is a need in the art for macromolecular matrices which can be manipulated to incorporate molecularly tailored polyhydroxylate sensing species and related calibration moieties in order to produce sensors having optimized characteristics. Embodiments of present invention fulfill these needs and provide other related advantages.

SUMMARY OF THE INVENTION

The present invention relates to polymer compositions and methods that are used for the determination of levels of polyhydroxylated compounds such as glucose. Embodiments of the invention include optimized polymer based sensors which produce a signal capable of detection that is modulated by the quantity of polyhydroxylated compound or analyte of interest. Typically such polymer sensors are implanted in the skin of a mammal such as a human. Generation of a signal by the amplification system is typically the result of interrogation by an optical source.

The invention disclosed herein has a number of embodiments. A preferred embodiment is a polymer composition including a fluorescent boronic acid of the general formula:

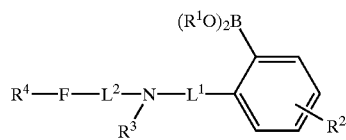

where F is a fluorophore (preferably Nile Blue), N is a nitrogen atom, B is a boron atom, $R^1$ is selected from the functional group consisting of hydrogen, aliphatic and aromatic groups, where the functional group $(R^1O)_2B$ is capable of binding glucose, $R^2$, $R^3$ and $R^4$ are optional and independent hydrogen, aliphatic or aromatic groups, further functionalized aliphatic or aromatic groups or groups that are capable of forming a covalent linkage to the polymer matrix (i.e. the scaffold or backbone core of the polymer composition), $L^1$ and $L^2$ are optional linking groups having from zero to four atoms selected from the group consisting of nitrogen, carbon, oxygen, sulfur and phosphorous. In highly preferred embodiments polymer composition further includes a reference fluorophore and the fluorescent boronic acid and the reference fluorophote are covalently coupled to the polymer matrix after polymerization. Polymers produced by these methods have a number of advantageous structural features. For example, such embodiments of the invention exhibit a number of advantageous properties including optimized calibration with a reference fluorophore as well as being highly soluble in an aqueous environment. Related embodiments of the invention include polymer compositions produced by a process of covalently coupling a fluorescent boronic acid and a reference fluorophore to a polymerized matrix. Other embodiments of the invention include methods for making these polymer compositions.

In typical embodiments of the invention, the polymer composition further includes an additional polymer that is coupled to the polymer matrix after polymerization. For example, the polymer composition can be a block copolymer. Alternatively, the additional polymer is grafted on to the polymer matrix. As is known in the art, the additional polymer can be any one of a variety of compounds used in such systems such as polyethyleneoxide compounds, polyethyleneoxide-polypropyleneoxide compounds and the like. In a specific embodiment of the invention, the polymer matrix is crosslinked with polymer compounds such as polyethyleneoxide or polyethyleneoxide-polypropyleneoxide. Preferably the additional polymer(s) enhance then swellability, biocompatibility and/or the hydrophilicity of the polymer composition.

The polymer compositions of the invention can be generated by protocols known in the art using the appropriate monomers. Alternatively a premade polymerized polymer matrix can be purchased. Typical polymers include polystyrene, polyvinylalcohol and the like. In addition, the fluorescent molecules of the invention can be covalently coupled to the polymer matrix using art accepted protocols such as those disclosed herein. An illustration of a number of typical covalent coupling reactions are shown in FIG. 20. In a preferred embodiment, the nitrogen atom in the fluorescent boronic acid is covalently coupled to the polymer matrix after polymerization via the group designated $R^3$. In a highly preferred embodiment of the invention, the group of atoms that links the nitrogen atom in the fluorescent boronic acid compound to the polymer matrix of the polymer composition enhance the solubility of the polymer composition.

Additional embodiments of the invention include sensors based on the polymer compositions disclosed herein as well as methods for determining analyte concentrations using these sensors.

DETAILED DESCRIPTION OF THE INVENTION

Figure 1:
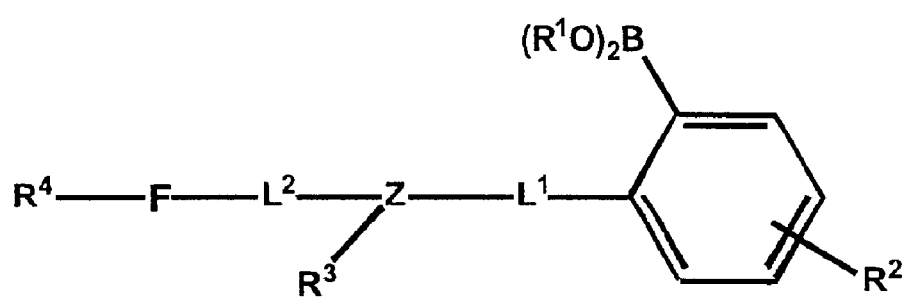
FIG. 1 shows a general chemical structure for a glucose sensing fluorescent boronate compound.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

1. Fluorescent Boronate Molecules Useful in the Detection of Polyhydroxylate Analytes Embodiments of the present invention include fluorescent compounds whose fluorescent properties are modulated by interactions with polyhydroxylate analytes. These compounds contain botonate moieties such as arylboronic acid functional groups, moieties which are used in the art as molecular recognition motifs to bind various polyhydroxylate analytes including glucose, galactose, fructose, mannose, maltose, cellobiose and lactose (see, e.g., Nakashima, et al., Chem. Lett. 1267 (1994); James, et al., J. Chem. Soc. Chem. Commun, 477 (1994); James, et al., Nature, 374:345 (1995); and Yoon, et al., J. Am. Chem. Soc., 114:5874 (1992) which are incorporated by reference herein).

Embodiments of the invention include optical biosensor systems that include these fluorescent compounds encompassed within a polymer matrix and methods of using these compounds to report on in-vivo levels of glucose. These compounds and systems are particularly useful in methods for the detection and measurement of in-vivo glucose concentrations via fluorescence. Related compounds and systems are described in U.S. Pat. No. 6,002,954, filed on Nov. 21, 1996, U.S. Ser, No. 09/663,567, filed on Sep. 15, 2000, U.S. Ser. No. 09/823,522, filed on Mar. 30, 2001, Ser. No. 09/826,745, filed on Apr. 4, 2001, U.S. Ser. No. 10/033,240, filed on Dec. 28, 2001 and U.S. Ser No. 09/953,563, filed on Sep. 12, 2001, which are herein incorporated by reference in their entireties.

Generalized biosensor molecules in accordance with embodiments of the invention include three components: (1) a fluorophore, (2) a linker moiety and (3) a boronate substrate recognition/binding moiety, which binds to polyhydroxylate analytes, such as glucose. These biosensor molecules further include a "switch" or "response" element that is drawn from electronic interactions that involve these components. This switch element is an integral component of the polyhydroxylate analyte sensing mechanism, i.e., transduction ability, of the biosensor molecules in accordance with embodiments of the present invention that serves to effectively "switch off" the fluorescence of the fluorophore in the absence of bound polyhydroxylate analyte. Thus, in the absence of polyhydroxylate analyte binding, e.g., glucose binding, the biosensor molecules in accordance with embodiments of the invention exhibit excited states of the fluorophore that are essentially quenched by the switch element. On the other hand, in the presence of a polyhydroxylate analyte fluorescence is greatly enhanced from the low level background levels that can be observed in the absence of analyte. Consequently, the binding of a polyhydroxylate analyte, such as glucose, can be correlated with the ambient analyte concentrations via a change in fluorescence intensity (see, e.g. U.S. Pat. No. 6,002,954 which is incorporated herein by reference) and/or a change in fluorescence lifetimes (see, e.g. U.S. Pat. No. 5,246,867, and U.S. patent application Ser. No 09/826,745 which are incorporated herein by reference).

In embodiments of the biosensor molecules of the invention, the fluorescent switch element generally includes the boron atom of the substrate recognition moiety and the hetetoatom of the linket moiety, preferably a nitrogen atom, and also includes the fluorophore in its electron-accepting capacity. This fluorescent switch is generally "off" in the absence of bound polyhyclroxylate analyte and is generally "on" in the presence of bound polyhydroxylate analyte. Thus, the reversible binding of a polyhydroxylate analyte essentially turns the fluorescent switch "on" and "off".

Although in the case of particular biosensor molecules, this switching function is not an "all or none" phenomenon, as a certain level of background fluorescence may be observed in the absence of polyhydroxylate analyte.

In one group of embodiments, the amplification components include an arylboronic acid moiety attached to an amine-functionalized fluorescent molecule. The linkage between the arylboronic acid moiety and the fluorescent molecule can typically be from about two to about four carbon atoms, preferably interrupted by one or more heteroatoms such as oxygen, sulfur, phosphorus or nitrogen. Certain non-limiting examples of suitable linkages include —$CH_2$—, —NH—$CH_2$—, —$(CH_2)_2$—NH—$CH_2$—, —C(O) $CH_2$—NH—$CH_2$—, —$CH_2$—NR—$CH_2$—, —$(CH_2)_2$—NR—$CH_2$—, and —C(O)$CH_2$—NR—$CH_2$—, in which the R group is an alkyl substituent of from 1 to about 8 carbon atoms. As used herein the term "alkyl" refers to a saturated hydrocarbon radical which may be straight-chain or branched-chain (for example, ethyl, isopropyl, t-amyl, or 2,5-ditnethylhexyl). This definition applies both when the term is used alone and when it is used as part of a compound term, such as "haloalkyl" and similar terms. Preferred alkyl groups are those containing 1 to 6 carbon atoms. All numerical ranges in this specification and claims are intended to be inclusive of their upper and lower limits. Additionally, the alkyl group which is attached to a nitrogen atom in the linkages can preferably be substituted with a functional group such as hydroxy, carbonyl, amino or thiol group etc. which can facilitate the covalent attachment of the amplification component to a biocompatible matrix.

FIG. 1 shows a preferred biosensor molecule in accordance with embodiments of the invention which includes the fluorophore denoted as F. In embodiments of the biosensor molecules of the invention, this fluorophore is the core fluorophore upon which substituents can be added to achieve desired electronic and/or chemical properties of a particular biosensor molecule. For example, substituents can be added that effect the absorption and emission wavelengths, the quantum yield and/or the fluorescence lifetimes of particular embodiments of the biosensor molecules. Additionally, substituents may be added that affect the solubility of the biosensor molecule and/or provide functionality that can be coupled to other molecules, such as a polymer matrix. The substrate recognition moiety of embodiments of the biosensor molecules is preferably provided by a phenylboronic acid moiety, namely, $(C_6H_5)B(OR^1)_2$, where $R^1$ is hydrogen, a lower aliphatic or aromatic functional group. Preferably, $R^1$ is hydrogen. However, other substituted boronic acids also may be used in embodiments of the biosensor molecules provided that upon polyhydroxylate binding the electronic and chemical effects at the boron atom are not adversely affected so as to alter the functional properties of the resultant biosensor molecule, as noted herein.

In these preferred embodiments of the biosensor molecules include a phenylboronic acid that is covalently bonded to an optional linkage, $L^1$, which is part of the linker moiety. This configuration is illustrated schematically in FIG. 1. Besides the $L^1$ linkage, the linker moiety also includes a heteroatom, labeled as Z, preferably a nitrogen, however, the linker moiety may include a different electron-donating atom, such as oxygen, sulfur or phosphorous. The linker moiety farther includes a second optional linkage, $L^2$, which provides a linkage to the fluorophore. The linkages $L^1$ and $L^2$ are each generally 0–4 contiguous atoms selected from carbon, oxygen, nitrogen, sulfur, and phosphorous, and preferably are simple alkyl chains where n=0, 1, 2, 3, 4, 5, 6, 7, 8, or the like. Additionally, preferred linkers may contain polyethylene oxide (PEO), hydroxy alkyl and amino alkyl groups. Optional groups $R^2$, $R^3$ and $R^4$ are attached respectively to the phenyl group, the heteroatom of the linker moiety, and the fluorophore. These optional groups may be functional groups that achieved desired electronic and chemical effects and/or that can form covalent linkages to a polymer matrix, or the like. $R^2$, $R^3$ and $R^4$ may be hydrogen, an aliphatic, aromatic, acidic, —$NH_2$, —OH, SH, or NCO functional groups or the like. In preferred embodiments, $R^3$ forms a covalent linkage to a polymer matrix.

In a highly preferred embodiment of the biosensor, the linkage $L^1$ consists of 1–2 (most preferably 1) carbon atoms and the linkage $L^2$ consists of 0 (most preferably) or 1 carbon atom and the fluorophore is Nile Blue (see, e.g. "LONG WAVE FLUOROPHORE SENSOR COMPOUNDS AND OTHER FLUORESCENT SENSOR COMPOUNDS IN POLYMERS (PD-0469) filed Dec. 28, 2001, Ser. No. 10/033,240). Additionally, preferred linkers may contain polyethylene oxide (PEO), hydroxy alkyl and amino alkyl groups. As noted herein, in these molecules, optional groups $R^2$, $R^3$ and $R^4$ are attached respectively to the phenyl group, the heteroatom of the linker moiety, and the fluorophore. These optional groups may be functional groups that achieved desired electronic and chemical effects or that can form covalent linkages to a polymer matrix, or the like. For example, the group of atoms linking the terminal end of $R^3$ to the heteroatom can include atoms that influence hydrophilicity such as oxygen atoms (e.g. the pentylalcohol and polyethylene glycol groups disclosed herein). As is know in the art and illustrated in Example 1 below, $R^2$, $R^3$ and $R^4$ may be any one of a wide variety of groups such as hydrogen, aliphatic, aromatic or acidic groups and can include a linker that is suitable for covalently linking the botonate molecule to the appropriate reactive group on the polymer (e.g. —COOH, —$NH_2$, —OH, SH, or NCO etc. disclosed herein).

Preferably, $R^1$ $R^3$ and $R^4$ are each independently hydrogen, hydroxy, acyl, C1–C4 alkoxy, halogen, thiol, sulfonic acid, sulfonamide, sulfinic acid, nitro, cyano, carboxylic acid, a C1–C12 alkyl group, a substituted C1–C12 alkyl group, a C1–C12 alkenyl group, a substituted C1–C12 alkenyl group, a C1–C12 alkynyl group, a substituted C1–C12 alkynyl group, aryl, substituted aryl, arylalkyl, substituted arylalkyl, amine, or substituted amine. For each of the substituted species herein, the substituents are preferably hydroxy, acyl, aryl, C1–C4 alkoxy, halogen, thiol, sulfonic acid, amnines, sulfonamide, sulfinic acid, nitro, cyano, carboxamide or carboxylic acid. In particularly preferred embodiments, $R^1$ $R^3$ and $R^4$ are each independently hydrogen, hydroxy, C1–C4 acyl, C1–C4 alkoxy, halogen, thiol, sulfonic acid, sulfonamide, nitro, cyano, carboxylic acid, a C1–C4 alkyl group, a C1–C4 alkenyl group, a C1–C4 alkynyl group, aryl, arylalkyl, or amine. Each of the $R^2$ symbols independently represents hydrogen or C1–C4 alkyl, or taken together the two $R^2$ groups form a C2–C5 alkylene chain. Preferably, the $R^2$ groups are both hydrogen.

Preferably, each of $L^1$ and $L^2$ independently represent a linking group having from zero to four contiguous atoms, preferably one to two. The linkig groups are preferably alkylene chains (e.g., methylene, ethylene, propylene, or butylene). Alternatively, the alkylene chains can have one or more of the carbon atoms replaced by a oxygen, nitrogen, sulfur or phosphorus, with the understanding that any remaining valences on the heteroatoms can be occupied by hydrogen, hydroxy groups or oxo groups. Preferably, the heteroatoms when present, are oxygen or nitrogen. The symbol Z represents a nitrogen, sulfur, oxygen or phosphorus. One of skill would understand that for those embodiments in which, for example, Z is oxygen, a substituent group such as $R^1$ will not be present. Additionally, as noted herein, any remaining valences on the hetetoatoms can be occupied by hydrogen, hydroxy groups or oxo groups. Most preferably, Z is nitrogen.

Preferably, the fluorescent dye is an anthracene, fluorescein, xanthene (e.g., sulforhodamine, rhodatine), cyanine, coumarin (e.g., coumarin 153), oxazine (e.g., Nile blue), a metal complex or other polyaromatic hydrocarbon which produces a fluorescent signal. Structures for some of the embodiments of the fluorophotes are provided in U.S. Pat. No. 6,002,954 to Van Antwerp et al., which is incorporated herein by reference, along with the excitation and emission wavelengths for each. Particularly preferred are long wavelength fluorescent dyes having emission wavelengths of at least about 450 nm, preferably from 450 to about 800 nm. Shorter wavelength dyes typically do not provide sufficient signal through the skin. As a result, shorter wavelength dyes are suitable fot applications in which interrogation and signal delivery is by means of a fiber optic. Preferred shorter wavelength dyes ate those having emission wavelengths of about 320 nm to about 450 nm.

In preferred embodiments of the invention disclosed herein, F emits at a wavelength greater than about 500 nm, a wavelength greater than about 550 nm, a wavelength greater than about 600 nm or a wavelength greater than about 650 nm. In highly preferred embodiments, the excitation wavelength for F is greater than about 550 nm, 600 nm or greater than about 625 nm. In this context, those skilled in the art understand that the excitation and emission wavelengths of such molecules are found over in a focused spectrum of wavelengths and do not occur at a single absolute point. Consequently, with molecules that, for example, have an emission maximum centered near 675 nm, it is therefore accurate to describe such molecules as typically emitting at a wavelength greater than about 675 nm. In addition, with molecules that, for example, have an excitation maximum centered near 625 nm, it is therefore accurate to describe such molecules in such terms as having an excitation wavelength that is greater than about 625 nm. For a general description of the properties of fluorescent molecules and fluorescent techniques, see "Introduction to Fluorescence Techniques" from the Handbook of Fluorescent Probes and Research Chemicals, portions of which can be found online at http://www.probes.com (specifically at http://www.probes.com/handbook/sections/0069.html).

Preferred embodiments of sensor molecules having a specific molecular formula as shown in FIG. 1 are those where the excitation wavelength for F is greater than about 600 nm. Such embodiments have a number of advantages over similar previously described molecules. For example, such molecules have the advantage of being excited at a wavelength outside of the ultraviolet spectra, and therefore are particularly suited for use in, for example, subdermally implanted optical glucose monitoring systems (See e.g. U.S. Pat. No. 6,011,984). In particular, ultraviolet light, which has a spectrum that extends up to, but not beyond 400 nm, is known to be able to induce cumulative damage to human skin (see e.g. Lavker et al., J. Invest. Dermatol., 108(1): 17–21 (1997) and Gasparro Environ. Health Perspect, 108 Sppl. 1: 71–78 (2000)). Consequently sensors designed to function with fluorophores having excitation wavelengths outside of this range can avoid potential problems associated with the use of fluorophores having excitation wavelengths which fall within a range that, in certain contexts, has been shown to induce cumulative damage to human skin. Moreover, because the matching of the peak excitation wavelength with an existing light source (such as an LED or diode laser) facilitates the generation and use of embodiments of the invention including their use in transdermally implanted glucose monitors, excitation wavelengths for F greater than about 400 nm have this additional advantage over similar previously described molecules.

Preferred embodiments of sensor molecules having a specific molecular formula as shown in FIG. 1 are those where the emission wavelength for F is greater than about 650 nm have a number of other advantages over similar previously described molecules, particularly in their ability to transmit a signal through a tissue such as skin. Specifically, the transmission through a few millimeters of skin increases logarithmically with wavelength—from 0.1% at 400 nm to almost 100% at 850 nm (see e.g. Optical-Thermal Response of Laser-Irradiated Tissue (A. J. Welch and M. J. C. van Gemert eds., Plenum Press) (1995); Francis A. Duck, Physical Properties of Tissue (Academic Press) (1990) and Abraham Katzir, Lasers and Optical fibers in medicine (Academic Press) (1993). Thus, the longer the wavelength, the greater the transmission through skin. Because of the significant increase in optical skin transmission at longer wavelengths, a practical glucose sensor using the fluorescent molecules described herein can operate more efficiently, more accurately, and with a greater signal-to-noise ratio.

The fluorescent boronate compounds used in this embodiment of the invention can be prepared by the methods described in the examples below or as is known in the art (see, e.g. U.S. Pat. No. 6,002,954). A typical synthesis scheme for a fluorescent boronic acid molecule is detailed in FIG. 4A. This synthetic scheme is extremely versatile, allowing the facile preparation of any number of fluorescent boronate compounds with a myriad of polymeric matrices. Alkoxy moieties may be used at tethers between the polymer and fluorescent boronic acids, thus enhancing the solubility of the glucose receptor. Solubility of these molecules should be directly observable post synthetic characterization by testing fluorescence of the compounds in solutions of PBS.

Figure 4A:
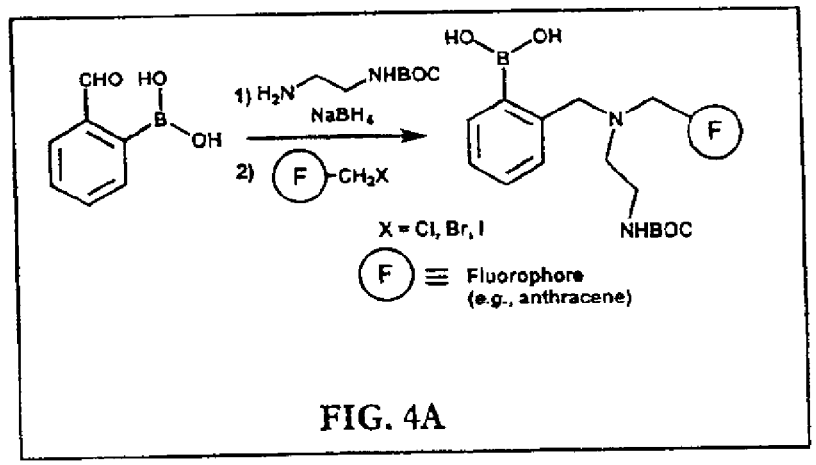
FIG. 4A provides a general scheme for the synthesis of a fluorescent boronic acid molecule that can be incorporated into a polymer.
Figure 4B:
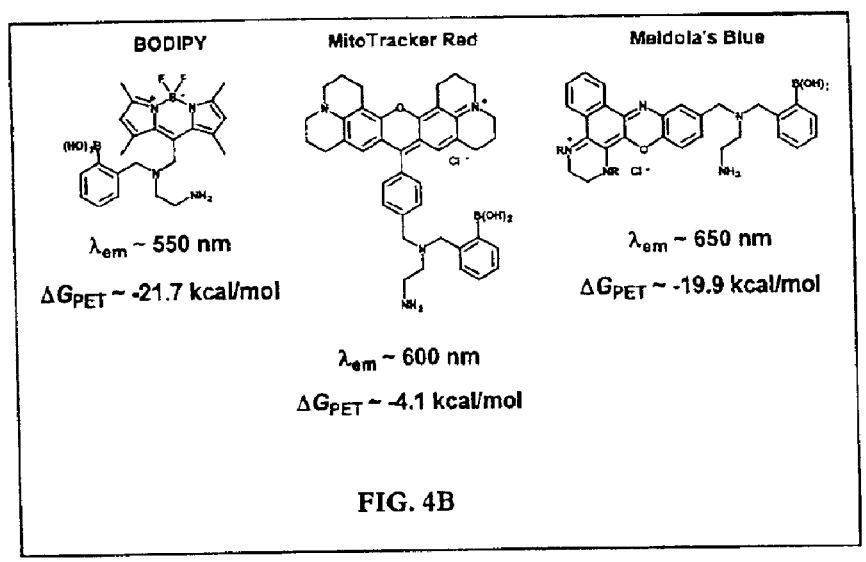
FIG. 4B shows illustrative longer wavelength fluorescent boronic acid targets for the optochemical glucose sensor.

In some embodiments of the invention, fluorescent boronic acids can be prepared using the methodology outlined in FIG. 4A. For example, BODIPY® methyl bromide (FIG. 4B) Molecular Probes B-2103, Eugene Oreg., is substituted for 9-chloromethylanthracene in the preparation of the BODIPY boronic acid derivative. Cyclic voltammetry data was collected (LLNL) for a number of fluorophores, and used to calculate the free energy of photoelectron transfer ($\Delta G_{PET}$) using the Rehm-Weller equation. This data provided the rationale for the choice of fluorophores. Three candidates are shown in FIG. 4B along with the calculated $\Delta G_{PET}$ values for the fluorophores. In this context, $\Delta G_{PET}$ values for the fluorophores can be used in methods to optimize sensor design (see, e.g. U.S. patent application Ser. No. 09/663,567).

Figure 5A:
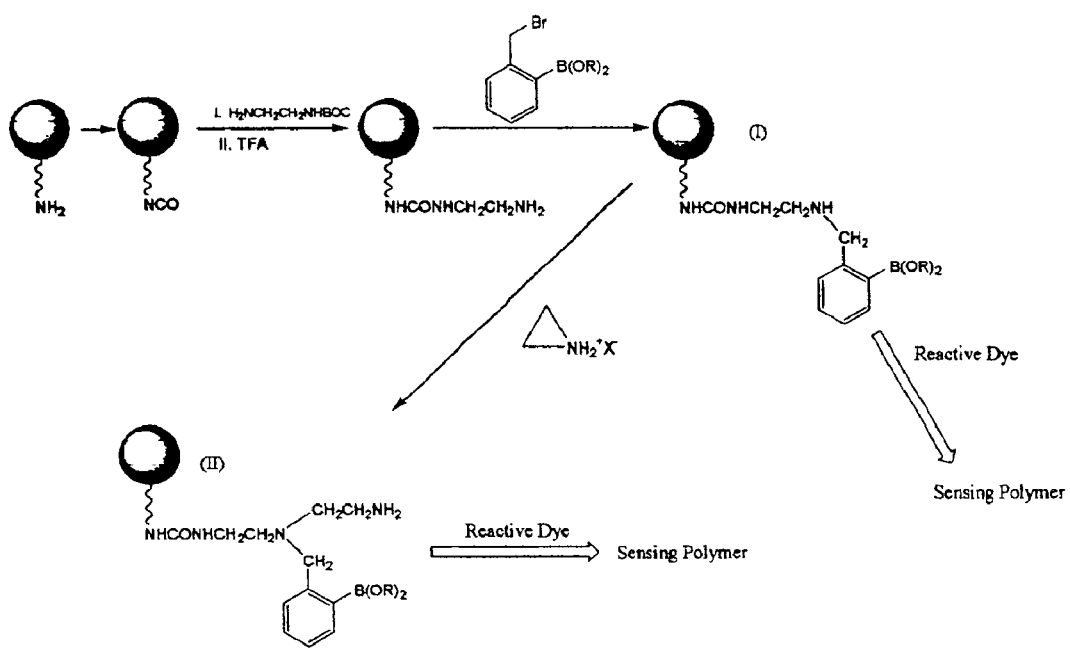
FIG. 5A details the synthesis of two solid supported boronic acids (I) and (II). Each material is prepared from an amino functionalized TentaGel™ (shown in the left-most schematic illustration). "Reactive dye" indicates fluorescent dye.

An alternative methodology that can allow for the rapid screening of fluorescent dyes is a solid supported synthesis of boronic acid precursors to glucochromatic sensors: compounds for the rapid screening of fluorescent dyes used in a fluorescent glucose sensor. This scheme allows for facile synthetic steps as a consequence of performing chemistry on the solid insoluble polymeric species. This also allows for rapid purification following a chosen chemical manipulation. In most instances purification is a matter of filtering the polymer and washing with the appropriate solvent. The synthetic methodology (in the preferred embodiment)

involves the placement of the glucose-binding unit (boronic acid) onto the solid support (polymer) prior to the placement of the fluorescent compound (dye). FIG. 5A details the synthesis of two solid supported boronic acids (I) and (II). Each material is prepared from an amino functionalized TentaGel (Rapp Polymere, e.g. the left most molecule in the schematic diagram in FIG. 5A).

Figure 5B:
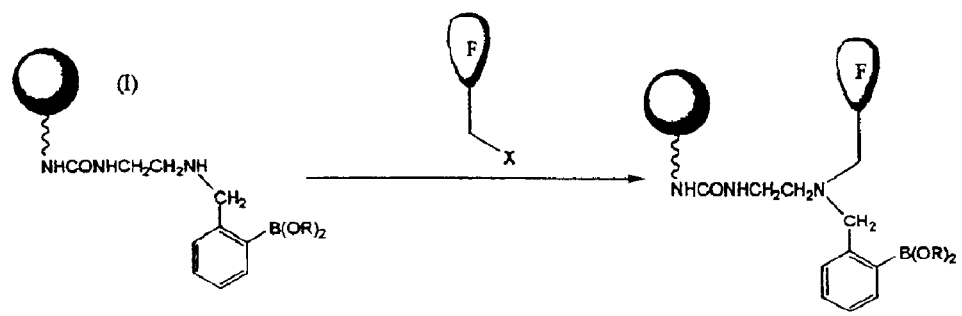
FIG. 5B illustrates how solid supported boronic acid (I) is a candidate for reactions with halomethylated fluorophores (or fluorophores that are conducive to chemistry that will provide a methylene group adjacent to the fluorophore).
Figure 5C:
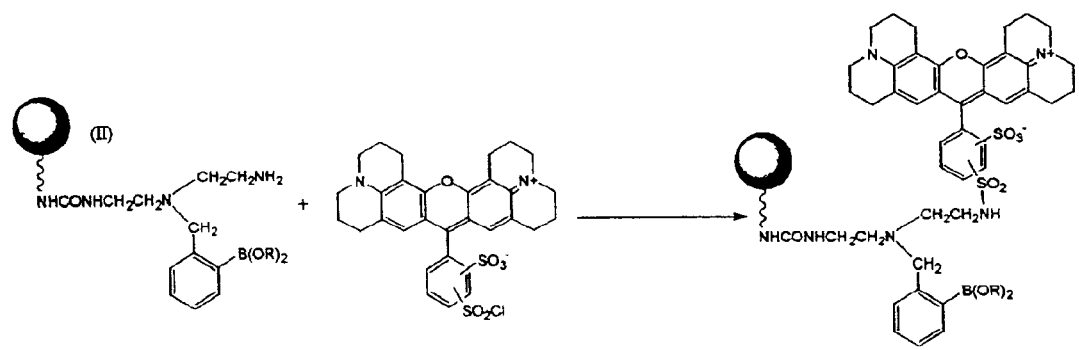
FIG. 5C illustrates how solid supported boronic acid (II) is different in that it has been designed to react with (primarily) an acid chloride or sulfonyl chloride compound such as Texas Red Sulfonyl chloride.
Figure 5D:
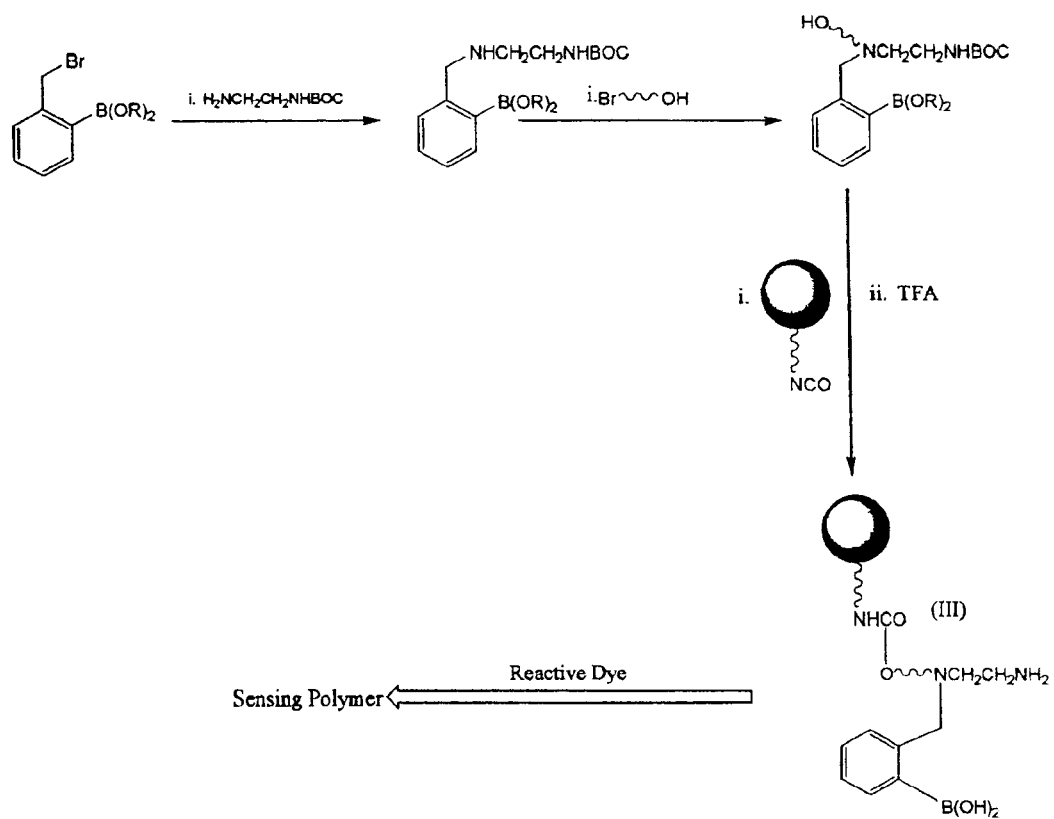
FIG. 5D details the preparation of solid supported boronate (III) which is similar to boronate (II) in that it is specifically designed to secure the dye via acylation chemistry or other appropriate functionalization.
Figure 5E:
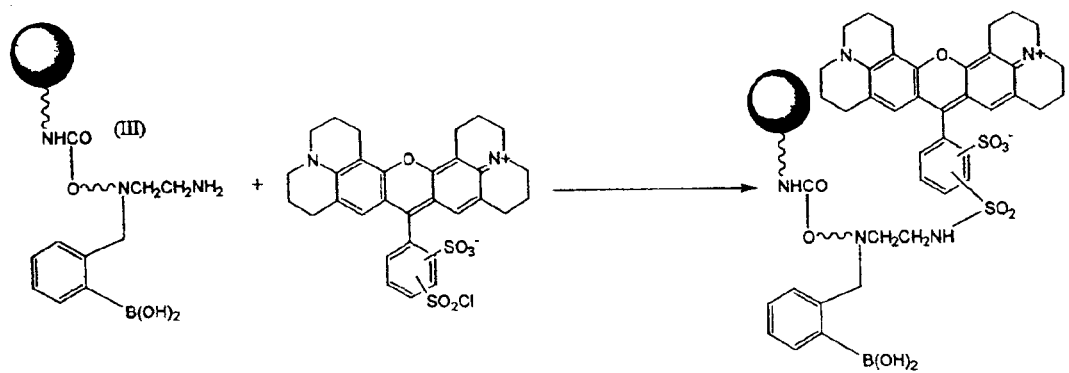
FIG. 5E details an example of acylation chemistry that can be performed on boronate (III) to yield a sold supported fluorescent boronate glucose sensor.
Figure 5F:
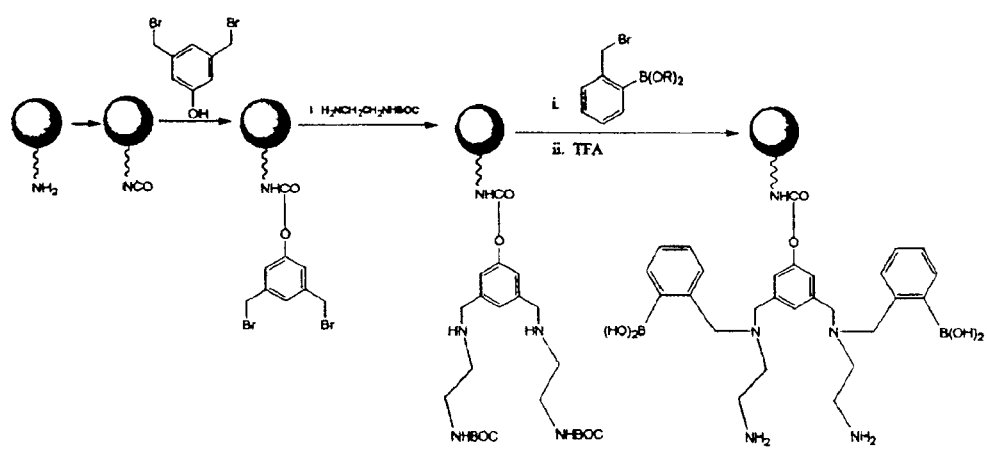
FIG. 5F details how this methodology may be utilized to prepare ditopic solid supported boronates.

In such solid supported fluorescent boronates schemes, solid supported boronic acid (I) identified as a candidate for reactions with halomethylated fluorophores (or fluorophores that are conducive to chemistry that can provide a methylene group adjacent to the fluorophore) as described in FIG. 5B. Solid supported boronic acid (II) is different in that it has been designed to react with (primarily) an acid chloride or sulfonyl chloride compound such as Texas Red Sulfonyl chloride as depicted in FIG. 5C. In addition, skilled artisans appreciate that amines can react with a variety of moieties and as such should not be limited to acylation chemistries. Solid supported boronate (III) is similar to boronate (II) in that it is specifically designed to secure the dye via acylation chemistry or other appropriate functionalization (FIG. 5D details the preparation of solid supported boronate (III)). FIG. 5E details an example of acylation chemistry that can be performed on boronate (III) to yield a solid supported fluorescent boronate glucose sensor. Finally it is worth noting that this methodology may be utilized to prepare ditopic solid supported boronates as detailed in FIG. 5F.

There are many possible variations on the synthetic "theme" of solid supported boronates as precursors to fluorescent-boronate-based glucose sensing molecules described herein and those shown herein are not all inclusive. Those depicted herein represent the genesis of the concept behind such molecular species. Furthermore, the use of TentaGel as a solid support is again only one example. Those skilled in the art understand that equivalent polymeric materials that possess appropriate characteristics to yield the desired materials.

Figure 6:
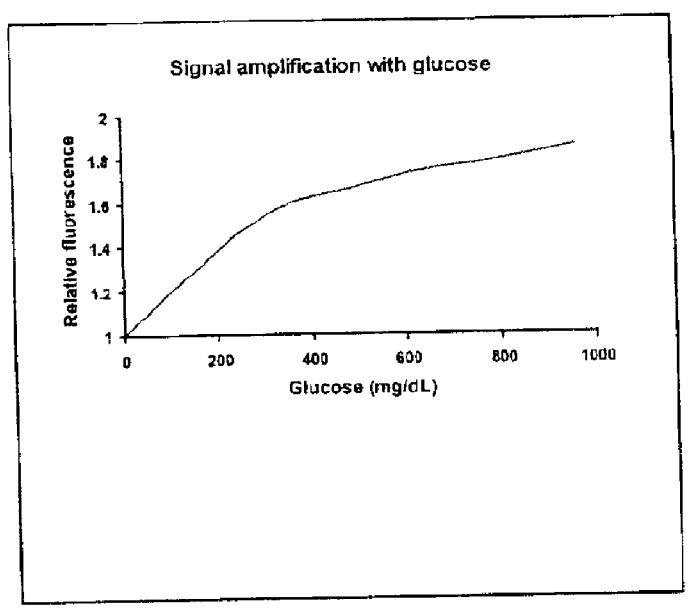
FIG. 6 provides a plot of relative fluorescence with changes in glucose concentration in mg/dL. This treated data is from the timescan in FIG. 13.

Following the preparation of each boronic acid derivative, complete compound characterization can be conducted by $^1$H NMR, IR, and electrospray MS and fluorescence spectroscopy (intensity & lifetime). Characterization by fluorescence spectroscopy can be conducted for all boronic acids in order to quantify the level of transduction for each new compound. Transduction experiments can be conducted at glucose concentrations of 100, 200, 300, 400 and 500 mg/dL in PBS. A plot of relative fluorescence with changes in glucose concentration in mg/dL is shown in FIG. 6.

2. Exemplary Polymers to Which Fluorescent Boronate Molecules Useful in the Detection of Polyhydroxylate Analytes can be Coupled For in vivo detection, it is advantageous to bind the boronic acid reporter species in a polymer matrix that prevent the diffusional loss of these species. Untethered or unencased species may diffuse into the body and in the worst case elicit toxic responses, or in the best case scenario be lost irrecoverably, thus making the detection of more of the analyte moot. Polymeric species can be naturally occurring, completely synthetic or modified naturally occurring materials. In addition to biocompatibility issues, such polymers preferably are soluble in PBS, that is, they are hydrophilic and either hydrogels or hydrogel-like species.

Still further, the polymer matrix should be prepared from biocompatible materials, or alternatively, coated with a biocompatible polymer. As used herein, the term "biocompatible" refers to a property of materials or matrix which produce no detectable adverse conditions upon implantation into an animal. While some inflammation may occur upon initial introduction of the implantable amplification system into a subject, the inflammation will not persist and the implant will not be rendered inoperable by encapsulation (e.g., scar tissue).

The biocompatible matrix can include either a liquid substrate (e.g., a coated dialysis tube) or a solid substrate (e.g., polyurethanes/polyureas, silicon-containing polymers, hydrogels, solgels and the like). Additionally, the matrix can include a biocompatible shell prepared from, for example, dialysis fibers, teflon cloth, resorbable polymers or islet encapsulation materials. The matrix can be in the form of a disk, cylinder, patch, microspheres or a refillable sack and, as noted, can further incorporate a biocompatible mesh that allows for full tissue ingrowth with vascularization. While subdermal implantation is preferred, one skilled in the art would realize other implementation methods can be used. A significant property of the matrix is its accessibility to analytes and other reactants necessary for chemical amplification of a signal. For example, a glucose monitoring matrix must be permeable to glucose. The implant should also be optically transparent to the light from the optical source used for interrogating the polysaccharide sensors. A typical amplification system can encompass a substrate layer, a transducer layer containing the amplification components, and a layer which is permeable to the analyte of interest.

The substrate layer be prepared from a polymer such as a polystyrene, polyvinylalcohol, polyurethane, silicone, silicon-containing polymer, chronoflex, P-HEMA or sol-gel. The substrate layer can be permeable to the analyte of interest, or it can be impermeable. For those embodiments in which the substrate layer is impermeable, the amplification components can be coated on the exterior of the substrate layer and futther coated with a permeable layer.

In addition to being biocompatible, another requirement for this outermost layer of an implantable amplification system is that it be permeable to the analyte of interest. A number of biocompatible polymers are known, including some recently described silicon-containing polymers (see, e.g. U.S. Pat. No. 5,777,060) and hydrogels (see, e.g. U.S. Pat. No. 6,011,984). Silicone-containing polyurethane can be used for the immobilization of most of the glucose binding systems or other analyte amplification components. Other polymers such as silicone rubbers (NuSil 4550), biostable polyurethanes (Biomer, Tecothane, Tecoflex, Pellethane and others), PEEK (polyether ether ketone) acrylics or combinations are also suitable.

In one group of embodiments, the amplification components can be attached to a silicone-containing polymer. This polymer can be a homogeneous matrix prepared from biologically acceptable polymers whose hydrophobic/hydrophilic balance can be varied over a wide range to control the rate of polyhydroxylated analyte diffusion to the amplification components. The matrix can be prepared by conventional methods by the polymerization of diisocyanates, hydrophilic diols or diamines, silicone polymers and optionally, chain extenders. The resulting polymers are soluble in solvents such as acetone or ethanol and may be formed as a matrix from solution by dip, spray or spin coating. Preparation of biocompatible matrices for glucose monitoring have been described in U.S. Pat. Nos. 5,777,060 and 6,011,984, the disclosures of which have been incorporated herein by reference.

The diisocyanates which are useful for the construction of a biocompatible matrix are those which are typically those which are used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3'-cyclohexane bis(methylene isocyanate) (H6 XDI), isophorone diisocyanate (IPDI) and 4,4'-methylenebis(cyclohexyl isocyanate) ($H_{12}$ MDI). In preferred embodiments, the diisocyanate is isophorone diisocyanate, 1,6-hexamethylene diisocyanate, or 4,4'-methylenebis(cyclohexyl isocyanate). A number of these diisocyanates are available from commercial sources such as Aldrich Chemical Company (Milwaukee, Wis., USA) or can be readily prepared by standard synthetic methods using literature procedures.

A second reactant used in the preparation of the biocompatible matrix described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol. As used herein, the term "poly(alkylene)glycol" refers to polymers of lower alkylene glycols such as poly(ethylene)glycol, poly(propylene)glycol and polytetramethylene ether glycol (PTMEG). The term "polycarbonate polyol" refers those polymers having hydroxyl functionality at the chain termini and ether and carbonate functionality within the polymer chain. The alkyl portion of the polymer can typically be composed of C2 to C4 aliphatic radicals, or in some embodiments, longer chain aliphatic radicals, cycloaliphatic radicals or aromatic radicals. The term "hydrophilic diamines" refers to any of the hydrophilic diols in which the terminal hydroxyl groups have been replaced by reactive amine groups or in which the terminal hydroxyl groups have been derivatized to produce an extended chain having terminal amine groups. For example, a preferred hydrophilic diamine is a "diamino poly(oxyalkylene)" which is poly(alkylene)glycol in which the terminal hydroxyl groups are replaced with amino groups. The term "diamino poly(oxyalkylene" also refers to poly(alkylene)glycols which have aminoalkyl ether groups at the chain termini. One example of a suitable diamino poly(oxyalkylene) is polypropylene glycol)bis(2-aminopropyl ether). A number of the polymers can be obtained from Aldrich Chemical Company. Alternatively, literature methods can be employed for their synthesis. The amount of hydrophilic polymer which is used in the present compositions can typically be about 10% to about 80% by mole relative to the diisocyanate which is used. Preferably, the amount is from about 20% to about 60% by mole relative to the diisocyanate. When lower amounts of hydrophilic polymer are used, it is preferable to include a chain extender.

Silicone polymers which are useful for the determination of polyhydroxylated analytes (e.g., glucose) are typically linear. For polymers useful in glucose monitoring, excellent oxygen permeability and low glucose permeability is preferred. A particularly useful silicone polymer is a polydimethylsiloxane having two reactive functional groups (i.e., a functionality of 2). The functional groups for such silicone polymers (as well as other non-silicone containing polymers such as polyvinyl alcohol and polystyrene) can be, for example, hydroxyl groups, amino groups or carboxylic acid groups, but are preferably hydroxyl or amino groups. In some embodiments, combinations of silicone polymers can be used in which a first portion includes hydroxyl groups and a second portion includes amino groups. Preferably, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA). Still others can be prepared by general synthetic methods known to those skilled in the art, beginning with commercially available siloxanes (United Chemical Technologies, Bristol, Pa., USA). For use in the present invention, the silicone polymers can preferably be those having a molecular weight of from about 400 to about 10,000, more preferably those having a molecular weight of from about 2000 to about 4000. The amount of silicone polymer which is incorporated into the reaction mixture can depend on the desired characteristics of the resulting polymer from which the biocompatible membrane are formed. For those compositions in which a lower analyte penetration is desired, a larger amount of silicone polymer can be employed. Alternatively, for compositions in which a higher analyte penetration is desired, smaller amounts of silicone polymer can be employed. Typically, for a glucose sensor, the amount of siloxane polymer can be from 10% to 90% by mole relative to the diisocyanate. Preferably, the amount is from about 20% to 60% by mole relative to the diisocyanate.

In one group of embodiments, the reaction mixture for the preparation of biocompatible membranes can also contain a chain extender which is an aliphatic or aromatic diol, an aliphatic or aromatic diamine, alkanolamine, or combinations thereof Examples of suitable aliphatic chain extenders include ethylene glycol, propylene glycol, 1,4-butanediol, 1,6-hexanediol, ethanolamine, ethylene diamine, butane diamine, 1,4-cyclohexanedimethanol. Aromatic chain extenders include, for example, para-di(2-hydroxyethoxy)benzene, meta-di(2-hydroxyethoxy)benzene, Ethacure 100™ (a mixture of two isomers of 2,4-diamino-3,5-diethyltoluene), Ethacure 300™ (2,4-diamino-3,5-di(methylthio)toluene), 3,3'-dichloro-4,4'diaminodiphenylmethane, Polacure™ 740 M (trimethylene glycol bis(para-aminobenzoate)ester), and methylenedianiline. Incorporation of one or more of the disclosed chain extenders typically provides the resulting biocompatible membrane with additional physical strength, but does not substantially increase the glucose permeability of the polymer. Preferably, a chain extender is used when lower (i.e., 10–40 mol %) amounts of hydrophilic polymers are used. In particularly preferred compositions, the chain extender is diethylene glycol which is present in from about 40% to 60% by mole relative to the diisocyanate.

In some embodiments, the polymer matrix containing the amplification components can be further coated with a permeable layer such as a hydrogel, cellulose acetate, P-HEMA, nafion, or glutaraldehyde. A number of hydrogels are useful in the present invention. For those embodiments in which glucose monitoring is to be conducted, the preferred hydrogels are those which have been described in U.S. Pat. No. 6,011,984. Alternatively, hydtogels can be used with the polymer matrix to encase or entrap the amplification components. In still other embodiments, the polymer matrix having the glucose sensing species can be covalently attached to a hydrogel.

Suitable hydrogels can be prepared from the reaction of a diisocyanate and a hydrophilic polymer, and optionally, a chain extender. The hydrogels are extremely hydrophilic and can have a water pickup of from about 120% to about 400% by weight, more preferably from about 150% to about 400%. The diisocyanates, hydrophilic polymers and chain extenders which are used in this embodiment of the invention are those which are described herein. The quantity of diisocyanate used in the reaction mixture for the present compositions is typically about 50 mol % relative to the combination of the remaining reactants. More particularly, the quantity of diisocyanate employed in the preparation of the present compositions can be sufficient to provide at least about 100% of the —NCO groups necessary to react with the hydroxyl or amino groups of the remaining reactants. For example, a polymer which is prepared using x moles of diisocyanate, can use a moles of a hydrophilic polymer (diol, diamine or combination), and b moles of a chain extender, such that x=a+b, with the understanding that b can be zero. Preferably, the hydrophilic diamine is a "diamino poly (oxyalkylene)" which is poly(alkylene)glycol in which the terminal hydroxyl groups are replaced with amino groups. The term "diamino poly(oxyalkylene" also refers to poly (alkylene)glycols which have aminoalkyl ether groups at the chain termini. One example of a suitable diamino poly (oxyalkylene) is polypropylene glycol) bis(2-aminopropyl ether). A number of diamino poly(oxyalkylenes) are available having different average molecular weights and are sold as Jeffamines™ (for example, Jeffamine™ 230, Jeffamine™ 600, Jeffamine™ 900 and Jeffamine™ 2000). These polymers can be obtained from Aldrich Chemical Company. Alternatively, literature methods can be employed for their synthesis.

The amount of hydrophilic polymer which is used in the present compositions can typically be about 10% to about 100% by mole relative to the diisocyanate which is used. Preferably, the amount is from about 50% to about 90% by mole relative to the diisocyanate. When amounts less than 100% of hydrophilic polymer are used, the remaining percentage (to bring the total to 100%) can be a chain extender.

Polymers of the invention can be made according to art accepted protocols. For example, polymerization of the hydrogel components can be carried out by bulk polymerization or solution polymerization. Use of a catalyst is preferred, though not required. Suitable catalysts include dibutyltin bis(2-ethylhexanoate), dibutyltin diacetate, triethylamine and combinations thereof. Preferably dibutyltin bis(2-ethylhexanoate is used as the catalyst. Bulk polymerization is typically carried out at an initial temperature of about 25° C. (ambient temperature) to about 50° C., in order to insure adequate mixing of the reactants. Upon mixing of the reactants, an exotherm is typically observed, with the temperature rising to about 90–120° C. After the initial exotherm, the reaction flask can be heated at from 75° C. to 125° C., with 90° C. to 100° C. being a preferred temperature range. Heating is usually carried out for one to two hours.

Solution polymerization can be carried out in a similar manner. Solvents which are suitable for solution polymerization include, tetrahydrofuran, dimethylformamide, dimethyl sulfoxide, dimethylacetamide, halogenated solvents such as 1,2,3-trichloropropane, and ketones such as 4-methyl-2-pentanone. Preferably, THF is used as the solvent. When polymerization is carried out in a solvent, heating of the reaction mixture is typically carried out for at least three to four hours, and preferably at least 10–20 hours. At the end of this time period, the solution polymer is typically cooled to room temperature and poured into DI water. The precipitated polymer is collected, dried, washed with hot DI water to remove solvent and unreacted monomers, then re-dried.

Additional illustrative examples of embodiments of the invention include carboxypolystyrene and polyvinylalcohol polymers with attached boronic acid fluorophore moieties are discussed in detail herein. While designed and used in different fashions, both polymers allow the continuous real-time signaling of glucose amounts as detailed herein. As is known in the art, similar protocols can be carried out with different attached fluorophores, with different modes of attachment to the polymer, and with differing arrangements of glucose binding moieties. Likewise, a those skilled in the art appreciate how other polymers such as carboxylated polymers can be used in a similar fashion either directly or grafted or blended with other polymers to form one of the variety of polymer species known in the art (e.g. copolymers, block copolymers etc.). Examples include, but are not limited to polyacrylic acid (PAA), polymethacrylic acid (PMAA), polymaleic acid (PMA), polylactic acid (PLA), polyglycolic acid (PGA), graft copolymers of PVA with PAA, and PVA with PMAA, copolymers of PMAA or PAA, acrylamide, vinylpyrollidone, PEG acrylates, PEG (methacry)ates, and other acrylates and acrylamides that are well known in this area.

3. Illustrative Examples of Polymers Functionalized with Fluorescent Boronate Motifs An implanted sensor where the sensing moiety is covalently coupled to a polymer matrix prevents the reactive species from diffusing into bodily fluids and being carried away, especially if the polymer material is insoluble via crosslinking or otherwise. Preferred polymeric materials have a adequate mechanical strength, is biocompatible and non-toxic. In addition, the glucose sensing boronate attached to a polymeric species preferably result in a species that mimics solution phase behavior with great fidelity. The literature is filled with examples of solution phase catalysts that either don't work on supports, or work with lesser efficiency.

Figure 7:
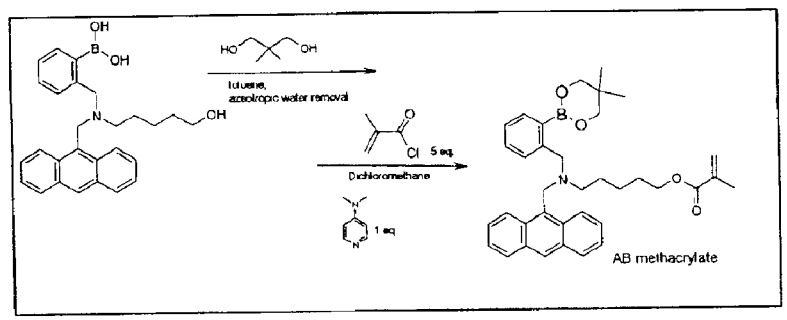
FIG. 7 provides a schematic of the synthesis of a pHEMA-AB Monomer.

Boronate species of the invention such as anthracene boronate can be covalently attached to a polymer at three different points, $R^2$, $R^3$ and $R^4$ (FIG. 1). One illustrative embodiment includes fluorescent boronate motifs attached at $R^3$ to pHEMA 2-hydroxyethylmethacrylate based polymers. The synthesis of this monomer is reported in FIG. 7. Photo- or chemical initiation produced a brittle material with poor mechanical properties. Transduction studies were performed by placing the material on a mesh and spiking the aqueous solution with glucose. An increase of ca. 60% was shown in PBS at a maximum concentration of 1000 mg/dL of glucose. This material was implanted into a rodent and is discussed in the experimental section below.

Figure 8:
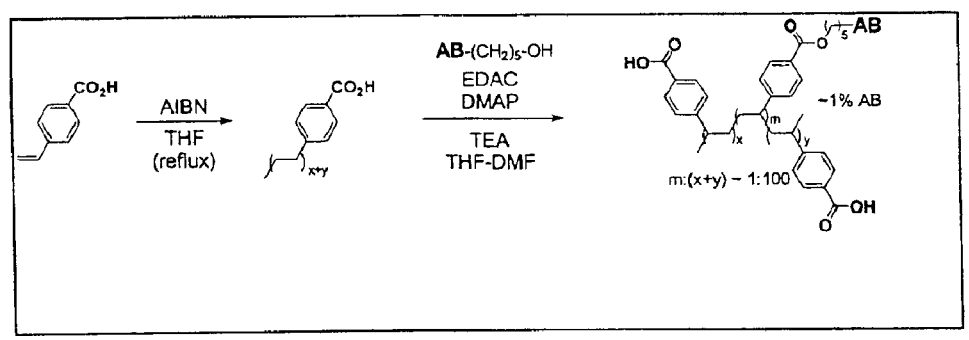
FIG. 8 provides a schematic of carboxypolystyrene containing ca. 1% AB; this polymer contains a carboxylic acid group on each monomer unit.

A preferred class of polymers for use with embodiments of the invention are the carboxylate-containing carboxy-polystyrenes. In such polymers there may be carboxylates at each monomer unit, or block co-polymers can be used. The carboxylate portion may be used as a graft or a blend, and play or relay not be cross-linked. The carboxylates enable ease of attachment of any species, with glucose binding molecules being only one good example. The glucose binding and the signaling portions may be attached to each other prior to fixing to the polymer, or they can be attached as individual pieces in close proximity to perform the same function. The catboxylates would also provide hydrophilicity and might well form hydrogels. Another illustrative hydrogel has been prepared from 4-vinylbenzoic acid, washed, and treated with ca. 1% pentylhydroxy AB via ester coupling (FIG. 8).

Figure 9:
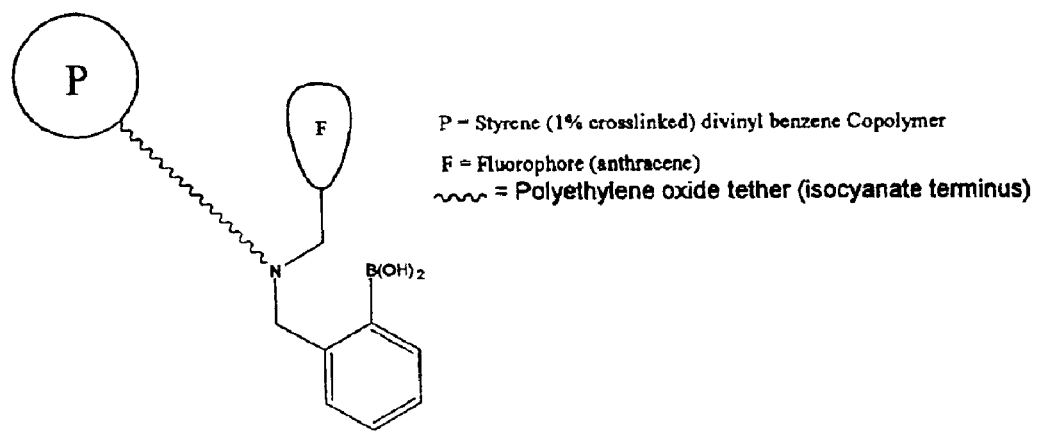
FIG. 9 provides a depiction of a fluorescent boronate generated via addition of the fluorescent boronic acid compound to a polymerized matrix (styrene divinyl benzene copolymer).

As noted herein, the disclosure herein further provides a series of polymeric materials which include styrene as a constituent of the polymeric backbone, a fluorescent boronate constituent for binding and sensing glucose, and a hydrophilic (tethering) constituent responsible for linking the fluorescent boronate and the macromolecule (polymer) are combined. In general, the class of compounds can be described by the structure detailed in FIG. 9.

Figure 10:
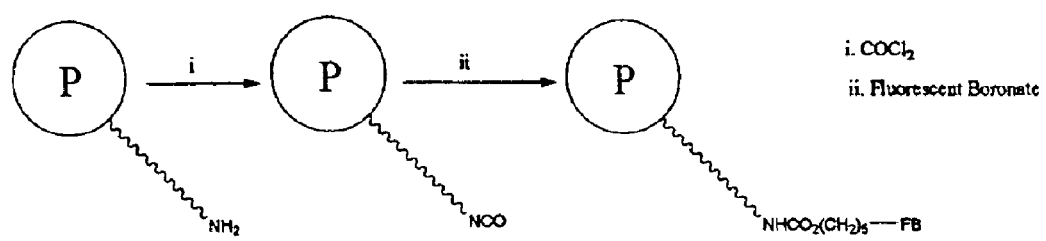
FIG. 10 provides a depiction of an illustrative synthesis scheme for generating a fluorescent boronate compound covalently coupled to a polymerized matrix.
Figure 11A:
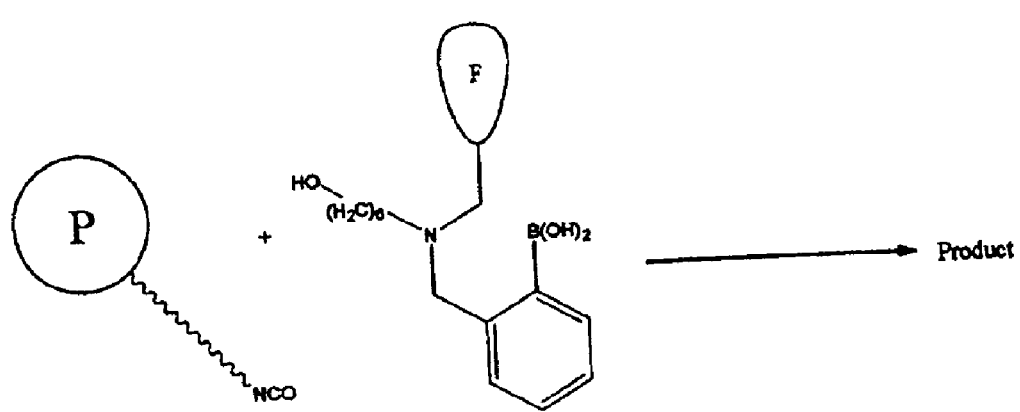
FIG. 11A illustrates typical chemistry associated with linking fluorescent boronate compounds to polymers.
Figure 11B:
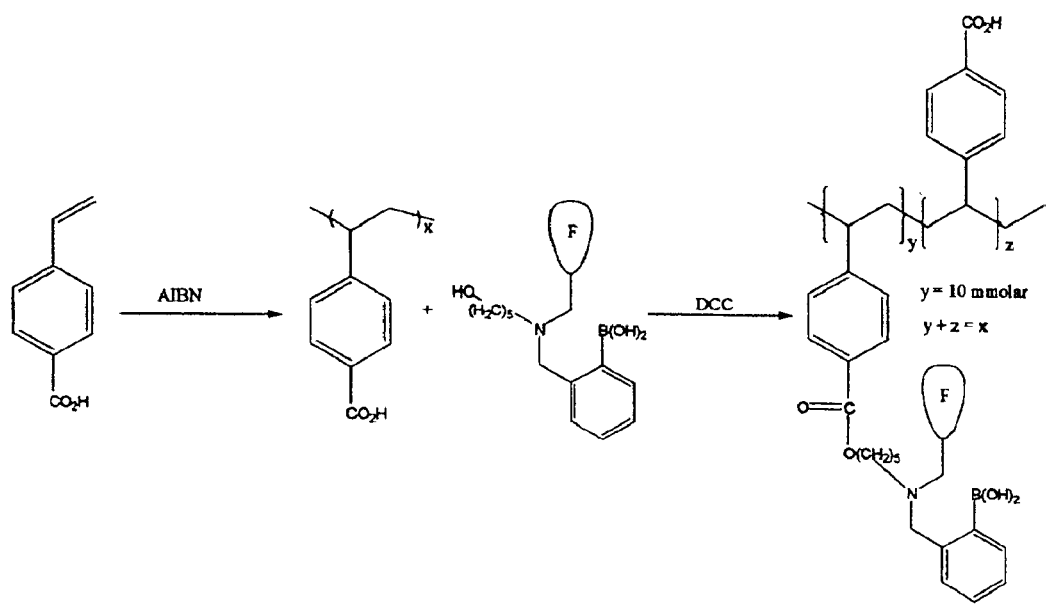
FIG. 11B illustrates typical chemistry associated with linking fluorescent boronate compounds to polymers.

A number of styrenic derivatives have been prepared for use with various embodiments of the invention. These include a modified TentaGel (Rapp Polymere). This polymer transduces glucose at a level of ~15–25% at 200–300 mg/dL of glucose solution. This solid-supported glucose sensor was prepared according to the synthesis depicted in FIG. 10 although other schemes can readily be devised. Other systems that have worked include polystyrene carboxylate that is esterified with hydroxypentyl anthracene boronate (represented as the fluorescent boronate in FIG. 11A) at a concentration of 10 mmole relative to free carboxylate. The synthesis of this material is outlined in FIG. 11B. This material has been shown to transduce glucose (where the fluorophore is anthracene) at a level of approximately 15%. This number represents the difference (increase) in fluorescence between complex (w/glucose) and the sensor in the absence of any glucose. Transduction measurements are reported for concentrations of 200 mg/dL glucose in PBS.

Figure 11C:
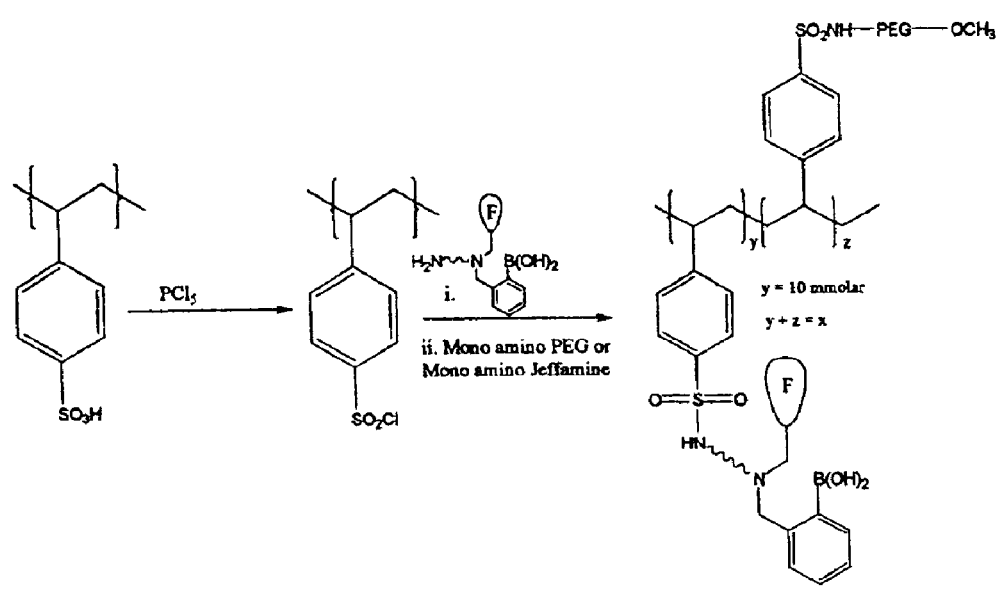
FIG. 11C illustrates typical chemistry associated with linking fluorescent boronate compounds to polymers.

Another styrenic polymer that has been investigated and should yield adequate transduction/response to glucose, (in light of polystyrene carboxylate), is a derivatized polystyrene sulfonic acid (FIG. 11C). Other options/manipulations available with this system include hydrolyzing any remaining sulfonyl chloride residues (to sulfonic acids) after the addition of an amine-containing reagent (or prior to such an addition). These acid residues provide the opportunity to prepare the sodium or potassium sulfonates (salts) so as to provide the polymer with hydrophilic domains (these functionalities are known to aggregate in this species).

4. Protocols for Linking Fluorescent Boronate Molecules to Polymers

Figure 4C:
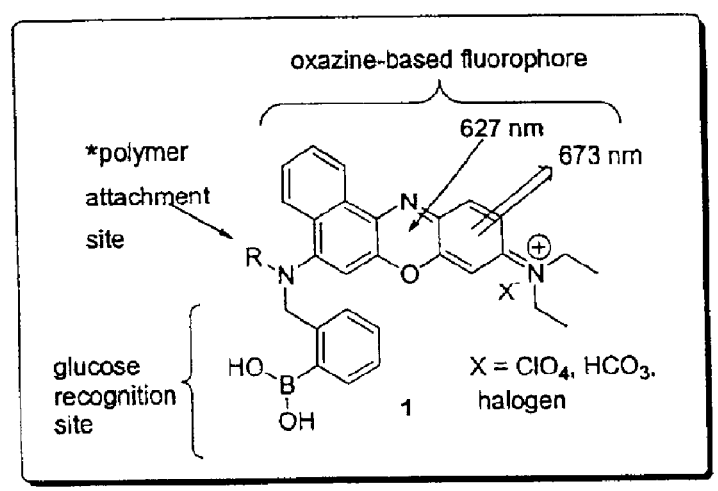
FIG. 4C provides an illustration of a typical oxazine-based boronate fluorophore (Nile blue) for glucose sensing.
Figure 12A:
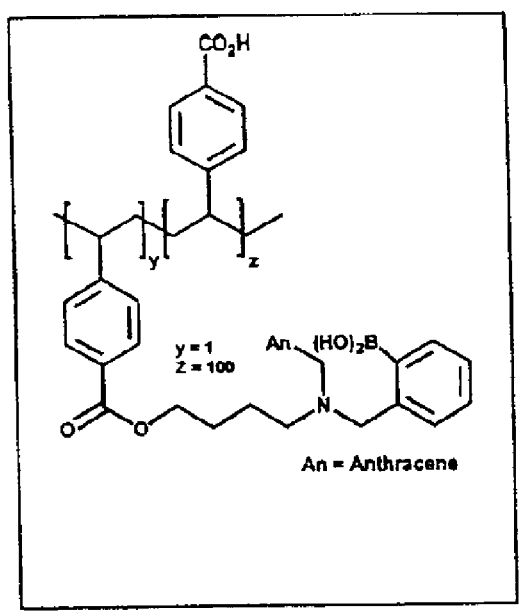
FIG. 12A shows a glucose sensing polymer with ca. 1% AB.

The data provided in herein (e.g. Example 1 below) effectively demonstrates how a fluorescent boronate motif (anthracene boronate) can be readily incorporated into the backbone of a polymer such as a 4-carboxystyrene homopolymer via the covalent coupling methods disclosed herein to yield a glucose sensing material (FIG. 12A) using the generic methodology outlined in FIG. 4. The syntheses of the polymer, and the polymer-FBA are straightforward and include the synthesis of a polymer and/or modification of a cormercially available polymer, rendering it amenable to an incorporation reaction with the FBA, and subsequent incorporation of the FBA into the polymer.

As disclosed herein, a wide variety of manipulations available with this system include the possibility of hydrolyzing any remaining reactive group residues such as sulfonyl chloride residues (to sulfonic acids) after the addition of an amine-containing reagent (or prior to such an addition). Such reactive group acid residues can also provide the opportunity to prepare the sodium or potassium sulfonates (salts) so as to provide the polymer with hydrophilic domains (i.e. these functionalities are known to aggregate in this species). Other manipulations possible following the addition of the fluorescent boronate include cross-linking of the matrices with reagents such as PEO or PEO-PPO diamine (ike Jeffamines™), hang tethered PEO or PPO diamines, or possibly cross-link available sulfonate groups (K+ or Na+) using $CaCl_2$.

Studies on how to optimize of the properties of polymers with glucose sensing species show that each specific process used to generate such embodiments of the invention produces functionalized polymer matrices having different material properties. Specifically, functionalized polymer matrices generated by a process where the polymer matrix are generated in a preliminary step and the various substituents of interest are added to the polymerized matrix in a subsequent step (as compared to a process of incorporating functionalzing components into the polymerization mixture during formation of the matrix) allows the production of functionalized polymer matrices compositions having a constellation of unique characteristics that are especially suited for sensing polysaccharides. As discussed herein, this constellation of characteristics includes the modulation of the glucose sensing species concentrations, the addition of reference fluorophores as well as the addition of functionalizing moieties that contribute to the overall hydrophilicity/aqueous nature of the final composition.

One characteristic of the polymer matrices disclosed herein is the inclusion of a reference fluorophore that is covalently coupled to the polymer matrix so that the environmental milieu of the reference fluorophore-polymer is analogous (e.g. mimics) to the environmental milieu of the fluorescent boronate compound-polymer. By carefully controlling the polymer designs in this manner, an optimized sensor is generated due to this specific manipulation of the reference fluorophore that is used as an internal control. Reference fluorophores are used in view of studies of the polymers generated herein that have demonstrated that their fluorescence properties can be effected external factors that are independent of analyte concentrations and that these factors can confound the determinations of analyte concentrations. In this regard, the reference fluorophore serves as an internal referencing system to correct for a number of factors, including background fluorescent signals, the orientation or position of the matrix relative to the sensing means as well as regionalized fluctuations in the concentration of the polysaccharide species in different regions of the polymer matrix. In this way, confounding changes in fluorescence intensity or the sensitivity of the sensing means is cancelled out.

In selecting the respective reporter (i.e. the fluorescent boronate compounds associated with glucose sensing) and reference fluorophores, the reporter fluorophore can have its degree of fluorescence modulated by external factors (e.g. glucose concentration), while the degree of fluorescence of the reference fluorophore should remain relatively constant. Preferably the reference fluorophore is selected so that it has a wavelength of excitation or emission spectrally removed from the wavelength representing the absorption maxima of the fluorophore associated with the glucose sensing boronate moieties. Preferably the fluorescence emitted by the second or reference fluorophore is a spectral region that does not overlap the absorption spectrum of the reporter species and is independent of the concentration of the absorbing species.

While protocols described in the art in which functional components of such a sensor are incorporated into polymerization mixture during formation of the matrix or are entrapped within the polymer matrix can be used to generate polysaccharide sensors, these protocols are not used to generate the optimized polymer compositions that are described herein. In particular, such procedures can create a level of structural unpredictability of the variety of components that make up the group of elements of the disclosed invention (including those having significantly different chemical properties) are either entrapped within a polymer matrix or combined together to be attached to their various reactive partners at the same time that the monomers in the mixture are being polymerized. In addition, certain reaction conditions required for polymerization (e.g. condensation-elimination and free radical polymerization) may alter some functional portions of the sensing molecules of the present invention including the fluorophore that is associated with the glucose sensing boronate complex which can alter the functional concentration of these attached molecules. Moreover, certain reaction conditions required for polymerization may also alter some functional portions the reference fluorophores of the present invention which can alter the functional concentration of these attached molecules. In addition, certain reaction conditions required for polymerization may alter functional portions of atomic groups that contribute to the overall hydrophilicity of the polymer matrix including the groups that tether the heteroatom to the polymer. In addition, certain reaction conditions required for polymerization may alter functional portions of hydrophilic molecules of the present invention that may be added to the polymer to, for example, contribute to the overall hydrophilicity of the polymer matrix. To overcome such problems, a process is described herein in which the polymer matrix is generated in a preliminary step and the various functional substituents are grafted on to the polymerized matrix in subsequent steps. This process produces functionalized polymer structures which have a unique constellation of characteristics.

As noted above, processes where a polymer sensor composition is produced by covalently coupling the fluorescent boronic acid and the reference fluorophore to an already polymerized matrix can be used produce functionalized polymer matrices having a number of optimized material properties. For example, such processes allow the reaction conditions at each step of the sensor synthesis to be carefully controlled. The control of reaction conditions then allows, for example, one to carefully control and determine the ultimate functional concentrations of fluorescent boronic acid and the reference fluorophore that are covalently attached to the polymerized matrix. This level of control over the coupling of the fluorescent boronic acids and reference fluorophores to the polymer provides for a concise determination of their relative amounts (e.g. their ratio) that are grafted onto the polymer matrix. The ability to control and determine this ratio then allows, for example, for the production of sensors having highly consistent and reproducible calibration properties. Polymer compositions having structures designed to generate sensors with highly consistent and reproducible saccharide sensing and calibration properties are advantageous for a number of reasons. For example, such sensors can be readily manufactured in a consistent manner. Moreover, sensors having such enhanced calibration properties can ultimately allow for more precise determinations of polysaccharide concentrations.

In addition, by covalently coupling the fluorescent boronic acid and the reference fluorophore together on the polymer matrix, such processes result in the incorporation of these functional moieties in a highly ordered manner that is not obtained when all of the moieties are combined together in a polymerization reaction or entrapped within the polymer matrix. This incorporation of the various functional moieties in a highly ordered manner then allows for uniform signal generation throughout the polymer matrix. Structures designed to produce a uniform signal throughout a polymer matrix are useful in reducing the effects of factors that can confound saccharine sensing.

As noted above, the matrix products disclosed herein are generated by a process in which the matrix is polymerized independently of the functional compounds (e.g. the boronate sensing fluorophore compounds, the fluorophore reference compounds, compounds which contribute to the hydrophilicity of the matrix etc.) and the functional compounds are then attached in steps subsequent to this polymerization procedure. By employing this process, a different final matrix product is produced which has a number of optimized characteristics including a structure in which the sensing fluorophore and the reference fluorophore are incorporated throughout the polymer in very similar environments within the matrix.

Processes in which the polymer matrix are generated in a preliminary step and the various substituents of interest ate added to the polymerized matrix in a subsequent step are also unique because they also allow the production of certain types of polymer structures such as block copolymers. Block copolymers are desirable in that the different blocks of functional residues in the polymer can have different properties, each of which is adapted for a specific function such as the covalent coupling of a glucose sensing species including those with tethers having hydrophilic residues, the covalent coupling of a reference fluorophore, the covalent coupling of independent hydrophilic groups that contribute to the aqueous nature of the polymer matrix etc.

Another characteristic of such an optimized polymer matrix is the modulation of the concentration of the polysaccharide sensing species in the matrix. As demonstrated herein, the concentration of fluorescent boronic acid (FBA) derivatives in the polymer is an important factor which can be modulated by the processes described herein. The best concentration of fluorescent boronic acid can be determined by screening the sensitivity of the polymer to standard glucose solutions in PBS and human plasma (100, 200, 300, & 400 mg/dL), and evaluating changes in the fluorophore lifetimes and populations, fluorescence intensity, and signal saturation, and signal/noise.

In addition, in the same manner that the polymer-FBA materials are prepared (FIG. 4) a polymer containing a reference fluorophore (polymer-REF) can be prepared and the reference fluorophore concentration optimized for the development of an intensity-based device.

5. Polymer Characterization & Glucose Transduction Experiments

Figure 12B:
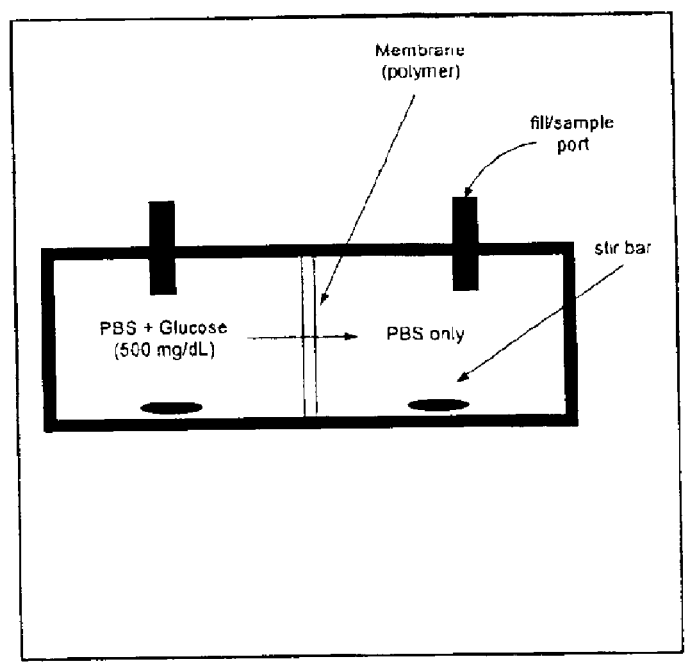
FIG. 12B illustrates a typical diffusion cell (Crown Glass) used to measure the permeability of glucose across a polymeric film.

Each of the polymer matrices described herein can be characterized using well-known techniques that include FTIR, fluorescence spectroscopy, and GPC. In addition, one can perform transduction experiments with glucose using fluorescence spectroscopy (lifetime and intensity measurements), and characterize the diffusion properties of the materials using a technique that has been developed for the study of the enzymatic glucose sensor membranes (FIG. 12B.) (see, e.g. U.S. Pat. No. 5,882,494). Typical protocols for such analyses are provided below.

Glucose Transduction Experiments

Glucose transduction experiments can be carried out by exposing a polymer film or polymer solution to standard glucose solutions of aqueous PBS and glucose solutions of human plasma then subsequently measuring changes in fluorescence intensity and fluorescent lifetimes while evaluating the changes as a function of glucose concentration. This data can provide for the development of in vitro calibration curves and the necessary understanding of the criteria associated with these types of experiments (linearity, offset and slope).

Diffusion Studies of Polymer-FBA Materials

In diffusion studies of polymer-FBA materials an organic solution of polymer can be filtered and spread onto a flat sheet of Teflon®. The solvent is removed by evaporation, leaving a thin film of polymeric material. The film is loaded into the diffusion cell interface clamp and the film is measured several times using a calibrated micrometer to determine the average thickness. The film is placed into the diffusion apparatus (FIG. 12B) and the left side is loaded with a PBS-glucose solution of 500 mg/dL ($PBS_{500}$). The right side is loaded with pure PBS ($PBS_0$) and the $PBS_0$ is sampled hourly and the concentration of glucose determined by taking 10 µL aliquot that is analyzed by a YSI Glucometer (Model 2700-S, Yellow Springs Instrument Company, Yellow Springs, Colo.). See, e.g., Example 3 below.

In case of polymer films, front face analysis is used to obtain lower scattering of light. Slit widths, and excitation and emission maxima are experimentally determined. Glucose additions are made after disconnecting the photomultiplier tube (PMT), and results in what appears as a drop in the reading in an apparent square wave manner with the intensity readings dropping to zero. Reconnecting the PMT shows either unchanged fluorescence or an increase indicating optical amplification as a result of signal transduction when the glucose interacts with the boronate entity. Such changes are followed and plotted to reveal the changes that occur in the signal with increasing amounts of glucose.

Tremendous progress has been made in obtaining signal transductions with fluorophores in aq. PBS at pH 7.4. The understandings obtained from this data have played and continue to play a tremendous role in the design and modification of polymer based florescence glucose sensing systems.

Figure 13:
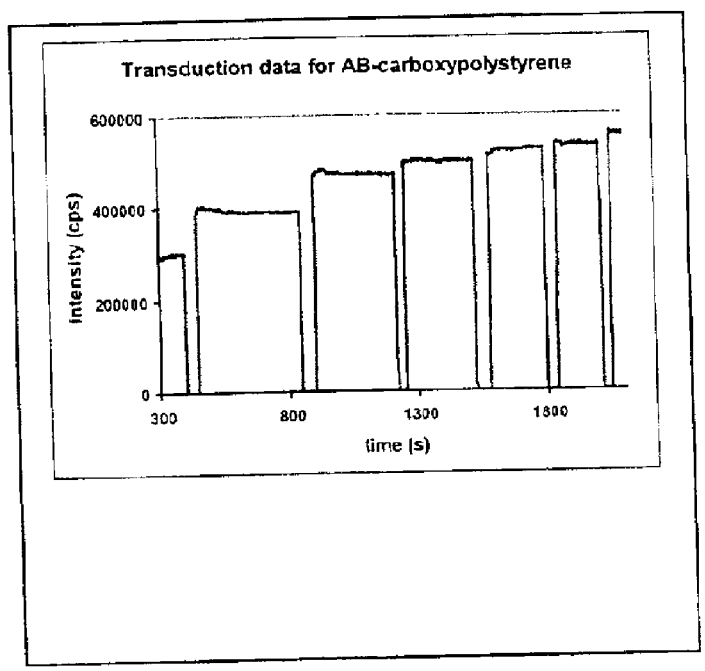
FIG. 13 provides time data for carboxy polystyrene with a higher AB content. Each glucose spike is ca. 160 mg/dL. Data is obtained out to approximately 950 mg/dL.
Figure 14:
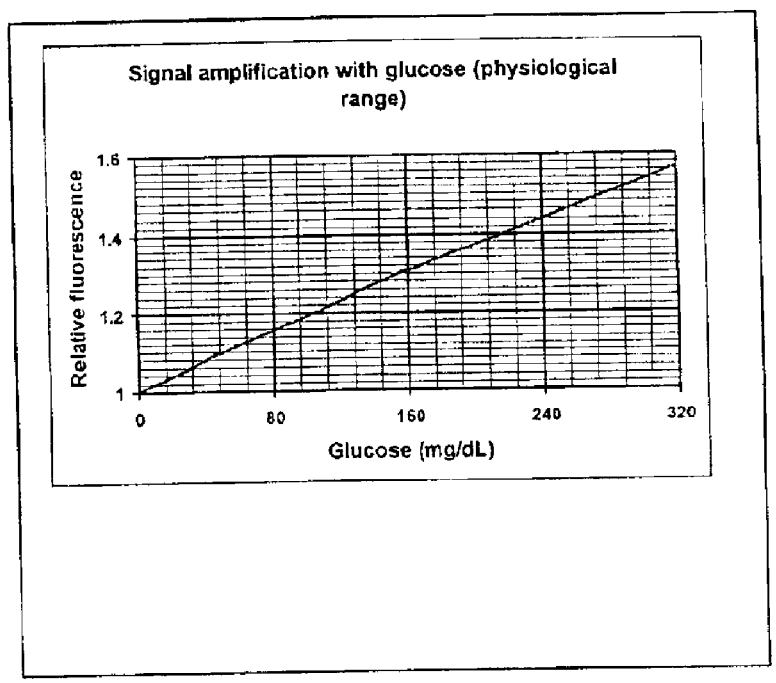
FIG. 14 provides an expansion of the initial section of FIG. 6. The data shows exceptionally well-defined linearity.

The methods provided herein in which the polymer is generated and the glucose sensing species in then added to this polymerized matrix allows the artisan to modulate the concentration of the glucose sensing species that is attached to the polymer which is an advantage over methods in which the glucose sensing species is added during the polymerization process. For example, such methods were used in the generation of a carboxypolystyrene matrix with a higher AB content. This higher AB content carboxypolystyrene is the best glucose transducing polymer to date. The complete timescan data going out to ca. 950 mg/dL glucose in ca. 160 mg/dL increments is shown in FIG. 13. If the data is plotted out simply as a relative signal amplification that occurs with increasing glucose, then it is seen that the plot is not linear (FIG. 13), except in the initial portion to about 330 mg/dL glucose (FIG. 14). The experiment has been reproduced with the same piece of film and just as a comparison to the solution phase data (using DMSO as spike solvent), the transduction obtained at ca. 200 mg/dL glucose is ca. 35%–40%.

The disclosure provided herein includes transduction tests in vitro with carboxystyrene polymer. The data for this polymer is presented again to show the evolution of this system in terms of the studies that were carried out. Presented in FIG. 13 is data that was obtained with this system with approximately 15% transduction at ca. 160 mg/dL glucose. Repeated tests, especially timescan data show 15% as the limit for transduction obtained at ca. 160 mg/dL glucose, with data dropping to between 5% and 10% transduction at the same glucose concentration.

Optimization of a Biocompatible Glucose Sensor of the Proper Size, Shape and Geometry that Functions Independent of Skin Thickness, Sensor Orientation, and Skin Pigmentation The data provided herein allows the selection of materials for animal testing and biocompatibility studies. The optimal implant design involves a number of interrelated issues: kinetics, signal-to-noise, mechanical integrity, palpability for implant removal, and biocompatibility.

Figure 16:
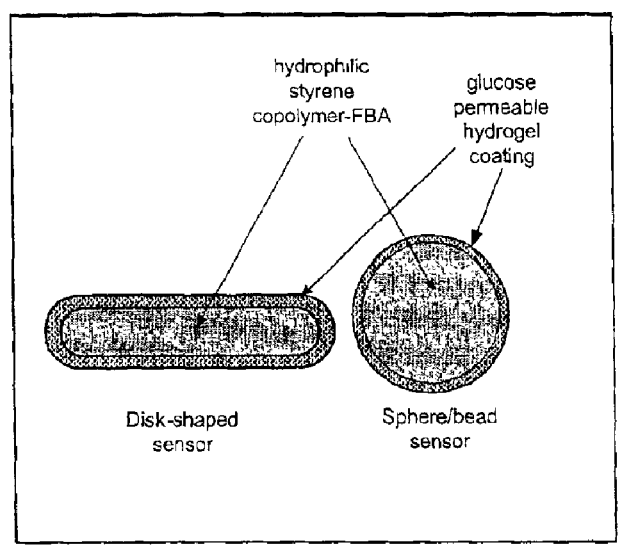
FIG. 16 shows two examples of possible optochemical sensor configurations.

Polystyrene copolymers are a preferred candidate. Polystyrene copolymers, in general, have excellent solubility in common organic solvents such as dichloromethane and tetrahydrofuran. These solvents are volatile and easily removed from the material after processing. There are several possible configurations for the final device. FIG. 16 shows two possible implant configurations for evaluation. Following the fabrication of each sensor implant, two separate in vitro fluorescence evaluations can be conducted. In an experiment designed to mimic the in vivo environment, a portable (Ocean Optics) spectrophotometer can be placed up against a sensor bead sitting inside of a section of intestinal membrane in a specified glucose solution. In addition, standard fluorescence experiments can be conducted with the aid of a Fluorolog® fluorescence spectrometer.

For in vivo studies, early functionality tests can be conducted in the rat. These studies can be used to evaluate the sensor's ability to track the rat's glucose during hyperglycemia and hypoglycemia events. Such experiments are described in detail below.

There is the possibility that certain polymers initially may not possess the optimal biocompatibility for a long-term implantable device. In such cases, biocompatibility studies as disclosed herein can provide the data for decisions about optimizing polymer implants. One configuration for a sensor embodiment of the invention (FIG. 16) places a hydrophilic styrene copolymer at the center and surrounded by a glucose permeable hydrogel for mininuzing protein adsorption (See, e.g. Wisniewski et al., Anal. Chem., 2000, 366: 617–619); Ellenbogen et al., *Pacing Clinical Electrophysiology*, 1999, 22, 39–48; and Rebrin et al.,. *Am.J.Physiol*. 1999, 277, E561-E57). Some of the materials that have been considered as an outer coating materials include polyurethanes, polyureas, acrylics, PEO, and alginate. Another method for improving biosensor biocompatibility (via mining inflammation) is local drug delivery at the biosensor surface. This strategy is employed today in pacemaker leads that deliver dexamethasone from the distal electrode. This approach has been shown to inimize threshold rise that occurs as a consequence of local edema, just after implantation.

6. General Embodiments of the Invention

Figure 3:
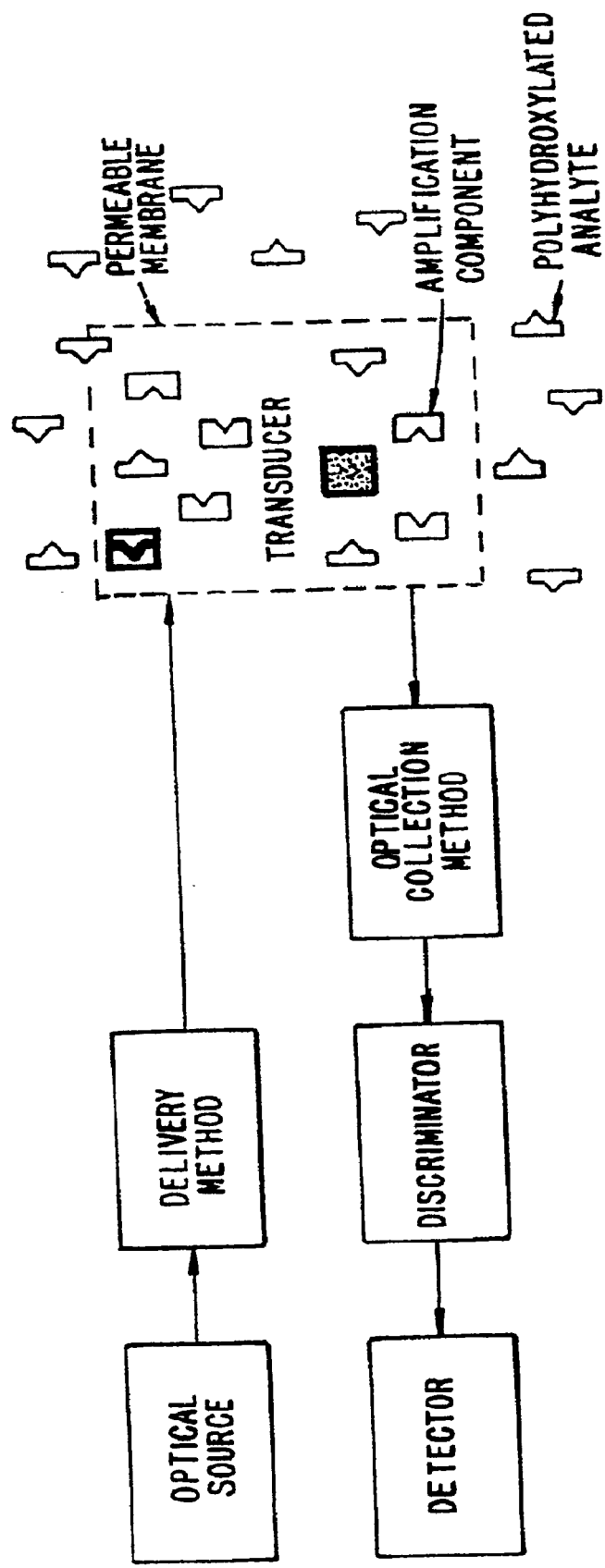
FIG. 3 illustrates a schematic of an optical analyte monitoring system which further illustrates the binding of a polyhydroxylated analyte to an amplification component following permeation into a biocompatible matrix.

A generalized comprehensive glucose sensor embodiment of the present invention is illustrated in FIG. 3. As can be seen, the basic scheme utilizes both a detector and source module which can be external to the skin. The source provides an excitation signal which interrogates a subcutaneous amplification system. The system then produces an amplified signal which is monitored by the external detector.

The amplification system can be implanted into a variety of tissues. Preferably, the system is implanted subcutaneously at a depth of from 1 to 2 mm below the surface of the skin. At this depth the system is most easily implanted between the dermis layer and the subcutaneous fat layer. These layers, in mammals are relatively easily separated and an amplification system (e.g., chemical amplification components in a biocompatible polymer) can be inserted into a small pocket created in a minor surgical procedure. The implanted system can be perfused by capillary blood and made of a material through which glucose can easily diffuse. Alternatively, the amplification system can be placed in contact with other fluids containing the analyte of interest.

In preferred embodiments (illustrated in FIG. 2), the amplification system contains an immobilized chemical amplification component, a fluorescent moiety which provides a signal which is modulated by the local analyte concentration and a reference fluorophore. A filter can also be incorporated into the system for the fluorescent photons (for those embodiments in which a fluorescent dye is used). The implanted amplification system is interrogated transdermally by a small instrument worn or placed over the implant. The small instrument contains a light source (e.g., a filtered LED) and a filtered detector (e.g., a photomultiplier tube, an unbiased silicon photodiode). The signal from the detector provides a continuous reading of the patient's analyte level which can also be used as input to, for example, an insulin pump or a visual reading for the patient. Alternative embodiments are described herein (e.g., use of a fiber optic for interrogation of the amplification system).

FIG. 3 provides yet another schematic which illustrates the amplification system. According to this figure, the amplification system includes a permeable membrane, a matrix for immobilizing the amplification components, and the amplification components themselves. The polyhydroxylated analyte can then permeate the matrix, bind to the amplification components and produce a signal upon interrogation which is collected, filtered and detected. The optical sources can be a variety of light sources (e.g. laser diode, LED) and the light can be delivered to the amplification system via delivery methods which can include lenses and fiber optics. Alternatively, the optical interrogation can take place with transdermal illumination. The resultant signal can be collected, again via a fiber optic or lens, and sent to the detector, with the optional use of an intervening filter or discriminator.

In one embodiment, a light source is positioned external to the skin and the amplification system is placed at or coated on the distal end of a fiber optic, which is inserted through the skin into a subcutaneous layer. The fiber optic serves to conduct the light from the source to the amplification system, and then collects the light emitted from the amplification system and conducts it back to the detector. In yet another embodiment, the light source is also implanted under the dermis. Upon interrogation of the polysaccharide sensors by the internal light source, the polysaccharide sensors provides a signal which is transdermally transmitted to an external detector. In still another embodiment, the light source and detector are both implanted under the dermis. The detector then provides transmission of the information to an output reading device which is external to the skin. Finally, for those embodiments in which glucose levels are determined, some embodiments of the invention are directed to coupling of the detector signal to an insulin pump system in a "closed-loop" artificial pancreas.

7. Optimized Polymer Matrices of the Invention and Methods For Making Them

The invention disclosed herein has a number of embodiments. A preferred embodiment is a polymer composition including a fluorescent boronic acid of the general formula:

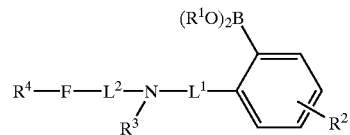

where F is a fluorophore (preferably Nile Blue), N is a nitrogen atom, B is a boron atom, $R^1$ is selected from the functional group consisting of hydrogen, aliphatic and aromatic groups, where the functional group $(R^1O)_2B$ is capable of binding glucose, $R^2$, $R^3$ and $R^4$ are optional and independent hydrogen, aliphatic or aromatic groups, further functionalized aliphatic or aromatic groups or groups that are capable of forming a covalent linkage to the polymer matrix (i.e. the scaffold or backbone core of the polymer composition), $L^1$ and $L^2$ are optional linking groups having from zero to four atoms selected from the group consisting of nitrogen, carbon, oxygen, sulfur and phosphorous. In highly preferred embodiments polymer composition further includes a reference fluorophore and the fluorescent boronic acid and the reference fluorophore are covalently coupled to the polymer matrix after polymerization. Such embodiments of the invention exhibit a number of advantageous properties including being soluble in an aqueous environment and producing a fluorescence signal that is modulated by the presence of glucose.

In typical embodiments of the invention, the polymer composition further includes an additional polymer that is coupled to the polymer matrix after polymerization. For example, the polymer composition can be a block copolymer. Alternatively, the additional polymer is grafted on to the polymer matrix. As is known in the art, the additional polymer can be any one of a variety of compounds used in such systems such as polyethyleneoxide compounds, polyrthyleneoxide-polypropyleneoxide compounds and the like. In a specific embodiment of the polymer matrix is crosslinked with polymer compounds such as polyethyleneoxide or polyethyleneoxide-polypropyleneoxide. Preferably the additional polymer(s) enhance the solubility of the polymer composition.

The polymer compositions of the invention can be generated by protocols known in the art using the appropriate monomers. Alternatively a premade polymerized polymer matrix can be purchased. Typical polymers include polystyrene, polyvinylalcohol and the like. In addition, the fluorescent molecules of the invention can be covalently coupled to the polymer matrix using art accepted protocols such as those disclosed herein. An outline of a number of typical covalent coupling reactions are shown in FIG. 20. In a preferred embodiment, the nitrogen atom in the fluorescent boronic acid is covalently coupled to the polymer matrix after polymerization via the group designated $R^3$. In a highly preferred embodiment of the invention, the group of atoms that links the nitrogen atom in the fluorescent boronic acid compound to the polymer matrix of the polymer composition enhance the solubility of the polymer composition.

A related embodiment of the invention is a polymer composition including a fluorescent boronic acid and a reference fluorophore; where the composition is produced by a process of covalently coupling the fluorescent boronic acid and the reference fluorophore to a polymerized matrix. As noted above, the specific process used to generate such embodiments of the invention produces functionalized polymer matrices having a number of beneficial material properties. Specifically, functionalized polymer matrices generated by a process where the polymer matrix are generated in a preliminary step and the various substituents of interest are grafted on to the polymerized matrix in a subsequent step (as compared to a process of incorporating functionalizing components into the polymerization mixture during formation of the matrix) allows the production of functionalized polymer matrices compositions having a constellation of unique characteristics that are especially suited for sensing polysaccharides.

In the polymer matrix products generated by this process the fluorescent boronic acid has the general formula:

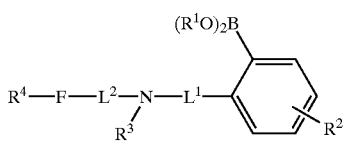

where F is a fluorophore (preferably Nile Blue), N is a nitrogen atom, B is a boron atom, $R^1$ is selected from the functional group consisting of hydrogen, aliphatic and aromatic groups, where the functional group $(R^1O)_2B$ is capable of binding glucose, $R^2$, $R^3$ and $R^4$ are optional and independent hydrogen, aliphatic or aromatic groups, further functionalized aliphatic or aromatic groups or groups that are capable of forming a covalent linkage to the polymer matrix, $L^1$ and $L^2$ are optional linking groups having from zero to four atoms selected from the group consisting of nitrogen, carbon, oxygen, sulfur and phosphorous. In highly preferred embodiments polymer composition further includes a reference fluorophore and the fluorescent boronic acid and the reference fluorophore are covalently coupled to the polymer matrix after polymerization. Such embodiments of the invention exhibit a number of advantageous properties including being soluble in an aqueous environment and producing a fluorescence signal that is modulated by the presence of glucose.

In preferred embodiments, the product produced by this process further includes an additional polymer that is coupled to the polymerized matrix. One illustrative product that is produced by this process (but not those in which the functionalizing components are included in the polymerization mixture during formation of the polymer) is a is a block copolymer. Alternatively, the additional polymer can be grafted on to the polymerized matrix.

As is known in the art, the additional polymer can be any one of a variety of compounds used in such systems such as polyethyleneoxide compounds, polyethyleneoxide-polypopyleneoxide compounds and the like. In a specific embodiment of the polymer matrix is crosslinked with polymer compounds such as polyethyleneoxide or polyethyleneoxide-polyptopyleneoxide. Preferably the additional polymer(s) enhance the solubility of the polymer composition.

The polymer matrix products of the invention can be generated by processes known in the art using the appropriate monomers. Alternatively a premade polymerized polymer matrix can be purchased. Typical polymers include polystyrene, polyvinylalcohol and the like. In addition, the fluorescent molecules of the invention can be covalently coupled to the polymer matrix using art accepted protocols such as those disclosed herein. An outline of a number of typical covalent coupling reactions are shown in FIG. 20. In a preferred embodiment, the nitrogen atom in the fluorescent boronic acid is covalently coupled to the polymer matrix after polymerization via the group designated $R^3$. In a highly preferred embodiment of the invention, the group of atoms that links the nitrogen atom in the fluorescent boronic acid compound to the polymer matrix of the polymer composition enhance the solubility of the polymer composition.

Yet another embodiment of the invention is a method of making a polymer composition including a fluorescent boronic acid and a reference fluorophore. Typically, the method includes the steps of covalently coupling the fluorescent boronic acid compound (see, e.g. FIG. 1) and the reference fluorophore to a polymerized matrix (one that has already been made). A variety of additional methods can be utilized to generate various embodiments of the invention disclosed herein. For example, methods of the invention can further including the step of covalently coupling an additional polymer to the polymerized matrix. Such polymers can be added to modulate the physical and chemical properties of the polymer compositions. For example, the additional of a hydrophilic polymer can be used enhance the solubility of the polymer composition. Such methods can be used to generate block copolymers or, alternatively, branched polymers (employing methods where the additional polymer is grafted on to the polymerized matrix). Alternatively methods for crosslinking polymer matrices can be used to generate additional embodiments of the invention.

As is known in the art, the polymer can be additional polymer can be any one of a variety of compounds used in such systems such as polyethyleneoxide compounds, polyethyleneoxide-polypropyleneoxide compounds and the like. In a specific embodiment of the invention, the polymer matrix is crosslinked with polymer compounds such as polyethyleneoxide or polyethyleneoxide-polypropyleneoxide. Preferably the additional polymer(s) enhance the solubility of the polymer composition.

The polymers of invention can be generated by methods known in the art, for example those using the appropriate monomers. Alternatively a premade polymerized polymer matrix can be purchased and the subsequent methods steps can be performed on this matrix. Typical polymers for use in such methods include polystyrene, polyvinylalcohol and the like.

The fluorescent molecules used in these methods of the invention can be covalently coupled to the polymer matrix via a number of methods such as those disclosed herein. An outline of a number of typical covalent coupling reactions are shown in FIG. 20. In a preferred embodiment, the nitrogen atom in the fluorescent boronic acid is covalently coupled to the polymer matrix after polymerization via the group designated $R^3$. Alternatively the fluorescent boronic acid is covalently coupled to the polymer matrix after polymerization via the group designated $R^2$. In a highly preferred embodiment of the invention, the methods are tailored for use with a group of atoms linking the nitrogen atom in the fluorescent boronic acid compound to the polymer matrix of the polymer composition that enhance the solubility of the polymer composition.

Yet another embodiment of the invention is a method of coupling a fluorescent boronic acid (FBA) compound to a polymerized matrix (PM) to generate a polymerized matrix composition (PMC). It will be apparent to the skilled artisan that such methods are used to generate various compositions disclosed herein. In these methods the fluorescent boronic acid compound has the general formula:

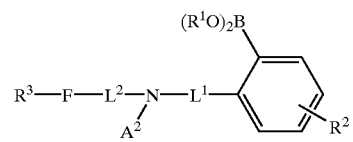

where F is a fluorophore (preferably Nile Blue), N is a nitrogen atom, B is a boron atom, $R^1$ is selected from the functional group consisting of hydrogen, aliphatic and aromatic groups, where the functional group $(R^1O)_2B$ is capable of binding glucose, $R^2$, $R^3$ and $R^4$ are optional and independent hydrogen, aliphatic or aromatic groups, further functionalized aliphatic or aromatic groups or groups that are capable of forming a covalent linkage to the polymer matrix, $L^1$ and $L^2$ are optional linking groups having from zero to four atoms selected from the group consisting of nitrogen, carbon, oxygen, sulfur and phosphorous. In these embodiments, $A^2$ is a reactive group on the FBA that is used to attach the fluorescent boronic acid compound to the polymer matrix; is used to attach the fluorescent boronic acid compound to the polymerized matrix and the resulting polymer composition (PMC) is produced by a reaction scheme:

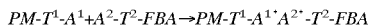

$$PM\text{-}T^1\text{-}A^1 + A^2\text{-}T^2\text{-}FBA \rightarrow PM\text{-}T^1\text{-}A^{1*}A^{2*}\text{-}T^2\text{-}FBA$$

where $A^1$ is a reactive group on the polymer matrix that is used to attach the polymer matrix to the fluorescent boronic acid compound, $T^1$ is the group of atoms that tethers the polymerized matrix to the terminal reactive group on the polymerized matrix that is used to attach the polymerized matrix to the fluorescent boronic acid compound, $T^2$ is the group of atoms that tethers the fluorescent boronic acid to the terminal reactive group on the fluorescent boronic acid that is used to attach the polymerized matrix to the fluorescent boronic acid compound and $A^{1*}$ $A^{2*}$ represents the group of atoms that link the polymerized matrix to the fluorescent boronate compound after the methodological steps used in their covalent attachment. In preferred embodiments of the invention, $T^1$ and $T^2$ include atoms that contribute to the solubility of the polymer composition.

8. Optical Systems of the Invention

Embodiments of the invention described herein also consist of optical systems for interrogating the polysaccharide sensors and detecting the signal thus produced by the polysacchatide sensors. As used herein, the term "interrogating" refers to illumination of the amplification components in the polysaccharide sensors and subsequent detection of the emitted light. One embodiment illustrating a transdermal optical system is shown in FIG. 2, where the light source (S) shines through the skin, and a detector (D) detects the fluorescence transmitted through the skin.

Figure 2:
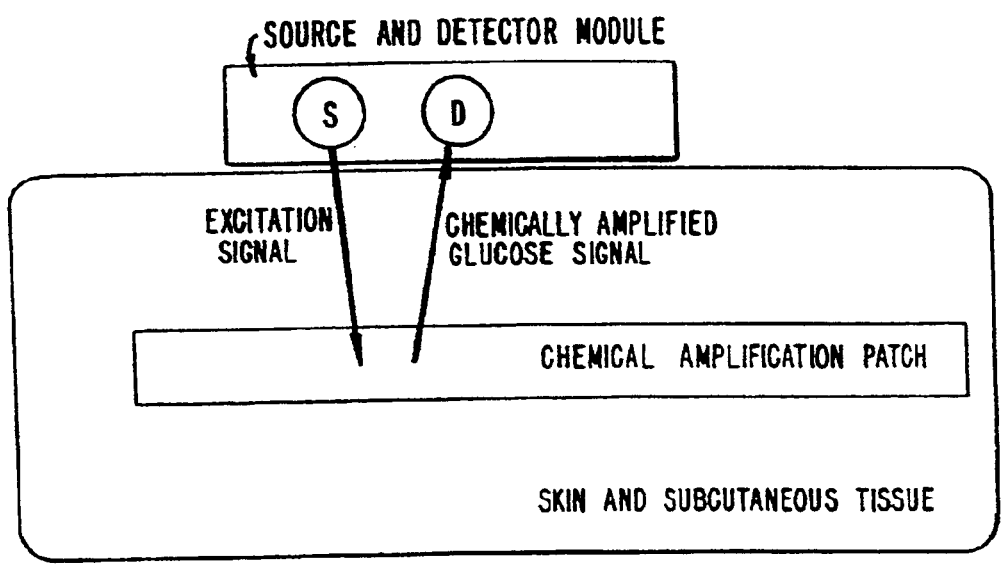
FIG. 2 shows a schematic of a typical optical glucose monitoring system.

FIG. 2 shows a schematic of the subdermally implanted optical glucose monitoring system. The light source (S) can be a lamp, an LED, or a laser diode (pulsed or modulated). The detector (D) can be a photodiode, CCD detector or photomultiplier tube. Optionally, filters are used to filter the incident and/or emitted beams of light to obtain desired wavelengths. The source and detector are shown in FIG. 2 as positioned outside the body, although the source and/or the detector can be implanted in a variety of configurations. The biocompatible material (e.g., silicone, polyurethane or other polymer) with the immobilized amplification components is implanted under the skin. The light source is used to illuminate the implanted system, and the detector detects the intensity of the emitted (fluorescent) light. Other modes of interaction may also be used, such as absorbance, transmittance, or reflectance, when the change in the amount of light or spectral character of the light that is measured by the detector or spectrometer is modulated by the local analyte (e.g., glucose) concentration. In yet other detection methods, the fluorescence lifetimes are measured rather than the light intensity.

With fluorescence, the ratio of intensity of excitation and emission can be used to quantify the glucose signal. In a preferred embodiment, the ratio of fluorescence from the amplification components to the fluorescence of a calibration fluorophore is measured. This method eliminates errors due to registration and variations of light transport through the skin (e.g., caused by different skin tones).

9. Methods for the Detection and Quantitation of Analytes

In view of the herein compositions and sensors, embodiments of the present invention also provide methods for the detection and quantitation of an analyte in vivo. More particularly, the methods involve quantifying the amount of a polyhydroxylated analyte in an individual, by: (a) interrogating a subcutaneously implanted amplification system with an energy source to provide an excited amplification system which produces an energy emission corresponding to the amount of the polyhydroxylated analyte; and (b) detecting the emission to thereby quantify the amount of the polyhydroxylated analyte in the individual.

The amplification and optical systems are essentially those which have been described herein, and the preferred embodiments including components of the biocompatible matrix (e.g., silicon-containing polymers, hydrogels, etc.) are also those which have been described herein. Prior to carrying out the present method, the amplification system is implanted in an individual using minimally invasive surgical or microsurgical techniques. The purpose of such implantation is to place in contact the amplification system and the analyte of interest (e.g., in fluid or tissue containing the analyte). Accordingly, the amplification system can be placed in or under the skin, or alternatively within an organ or blood vessel. When transdermal interrogation is used, the amplification system is preferably placed subcutaneously about 1–2 mm below the skin surface. For fiber optic mediated interrogation, the depth can be from 1–4 mm below the skin surface. For those embodiments in which the optical system and amplification components are in communication with an insulin pump, the placement can be at even greater depths.

The polyhydroxylated analyte can be any of a variety of endogenous or xenobiotic substances which have two or more hydroxy functional groups in positions vicinal to each other. Preferably, the analyte is a sugar, more preferably glucose.

Although the sensor matrices for polysaccharides like glucose are of primary interest for biomedical applications, the present sensor/transducer scheme is useful more generally for the measurement of other cis-diols. For example, the present sensor molecules have utility in the measurement of ethylene glycol contamination in boiler waters, where ethylene glycol contamination is an indication of heat exchanger tube degradation as well as other uses in similar contexts (see e.g. U.S. Pat. No. 5,958,192). These sensor molecules, can be of use in industrial fermentation processes (e.g. beer and wine), or in any number of process points in the production of high fructose corn syrup such as. enzyme reactors and the like (see e.g. U.S. Pat. No. 5,593,868; U.S. Pat. No. 4,025,389; Ko et al., Biotechnol. Bioeng. 57(4): 430–437 (1998) and Mou et al., Biotechnol. Bioeng. 18(10): 1371–1392 (1976)). Moreover, sensor molecules described herein exhibit characteristics which them particularly suited for uses such as the monitoring of industrial fermentation processes. In addition, as these compounds have the ability to bind saccharides, they can also be used qualitatively as sensors for carbohydrate molecules found in the cell surfaces of bacteria (see, e.g., Burnett et al., Biochem. Biophys. Res. Comm. 96(1): 157–162 (1980). Such sensors areuseful, for example, for identifying the presence of bacterial contamination in a number of environments.

In order that those skilled in the art can more fully understand embodiments of this invention, the following examples illustrating the general principles for preparation of polysaccharide responsive systems ate set forth. These examples are given solely for purposes of illustration, and should not be considered as expressing limitations unless so set forth in the appended claims.

EXAMPLES

Example 1

Illustrative Polymer Synthesis & FBA Incorporation

Disclosed herein is the design and implementation of a carboxylate polymer with a covalently bound boronate fluorophore conjugate capable of binding and signaling the amount of glucose under aqueous physiologically relevant conditions. Within the class of carboxylate containing polymers, one example would be that of a carboxylated polystyrene. The $AB(CH)_5$—OH is only of a variety of glucose binding and signaling species that might be attached through the carboxylates on the polystyrene. FIG. 8 illustrates the formation of this polymer and the subsequent attachment of the fluorescing glucose reporting species.

Polymer Synthesis & FBA Incorpotation

Given the successful demonstration of glucose sensing, in vitro, with poly(4-carboxystyrene)-anthracene boronic acid (FIG. 12A), the choices of polymer for the next generation of sensor material are quite meaningful and rational. The primary approach uses a styrenic copolymer as the matrix for attachment. The material properties considered when evaluating a new material include: mechanical integrity at 100% hydration, solubility for post synthetic processing, autofluorescence of the material, biocompatibility, and glucose permeability.

Figure 17:
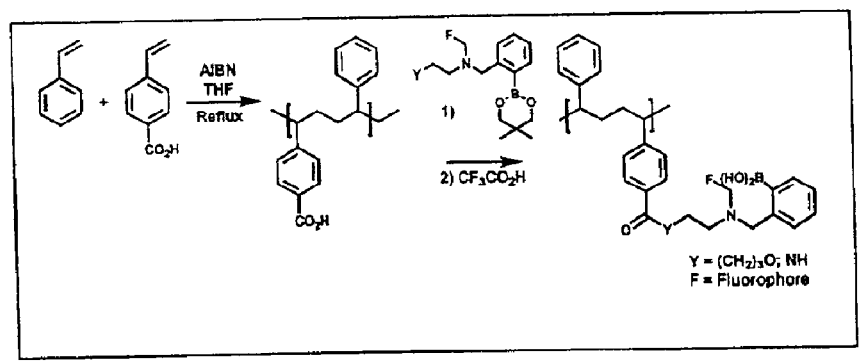
FIG. 17 shows a typical synthesis of carboxystyrene polymers.

The promising transduction results obtained for an AB-functionalized 4-carboxystyrene homopolymer with glucose is the impetus behind the decision to work with hydrophilic styrene-based polymers and copolymers that contain fluorescent boronic acid (FBA) groups. The scheme in FIG. 17 provides the method for preparing a FBA containing styrene-(4-carboxystyrene) copolymer will have improved solubility and mechanical properties over the 4-carboxystyrene homopolymer. The matrix presented in Table 1 below provides an iterative matrix of materials to maximize the efforts in this area.

| Styrene-Based Polymers | Fluorescent Boronic Acid (FBA) Derivatives | | |
| --- | --- | --- | --- |
| | BODIPY ® | Mito Tracker Red ® | Meldola's Blue |
| 10:90 Styrene: 4-Carboxystyrene Copolymer | X | X | |
| 25:75 Styrene: 4-Carboxystyrene Copolymer | | X | X |
| Sulfonated Styrene-Ethylene Copolymer | X | | X |
| Sulfonated Styrene-Ethylene-Butylene-Styrene (SEBS) Triblock Copolymer | X | X | X |

Formulation of Next Generation Polymers that have Imported Water Solubility and Contain Fluorescent Boronic Acid Derivatives for Glucose Sensing.

Subtle changes in material composition can result in unforeseen effects on material properties and characteristics (i.e., glucose permeability, biocompatibility/biofouling). This may limit the approach to glucose sensing using a solid-state matrix and in response to this, other approaches as reported in the literature that mimic solution-state behavior may provide reasonable alternatives (see, e.g. Ballerstadt et al., Anal. Chem. 2000. 72:4185–4192).

Some transformations that have been utilized in the attachment of the FBA to the polymer are detailed in Table 2 below. As disclosed herein, all of the synthetic sequences utilized are carried out on the polymer during the final step in order to minimize damaging the fluorophore to repeated chemical transformations in the overall synthesis.

TABLE 2

Methods for Attaching FBA Into Polymer Matrix.

| Polymer Reactive Group[a] | Transformation Reagent[b] | FBA-Reactant[c] | Resulting Product Linkage |
| --- | --- | --- | --- |
| Polymer-$SO_3H$ | $PCl_5$ | $RNH_2$ | Polymer-$SO_2NHR$ (sulfonamide) |
| Polymer-$CO_2H$ | $SOCl_2$ | $RNH_2$ | Polymer-CONHR (amide) |
| Polymer-$CO_2H$ | $SOCl_2$ | ROH | Polymer-$CO_2R$ (ester) |
| Polymer-$CO_2H$ | DCC | $RNH_2$ | Polymer-CONHR (amide) |
| Polymer-$CO_2H$ | DCC | ROH | Polymer-$CO_2R$ (ester) |
| Polymer-$NH_2$ | $COCl_2$ | $RNH_2$ | Polymer-NHCONHR (urea) |
| Polymer-$NH_2$ | $COCl_2$ | ROH | Polymer-$NHCO_2R$ (carbamate) |

[a] Polymers represent styrene family
[b] 25° C.; DMF or THF
[c] R = FBA derivative.

Example 2

Illustrative Protocol for the Incorporation of Pentylhydroxy AB into Carboxypolystyrene Carboxypolysyrene. A 10-mL, one-necked teat drop shaped flask equipped with a stirring bar, a reflux condenser, and a nitrogen inlet adaptor was charged with 4-vinylbenzoic acid (0.296 g, 2.00 mmol), AIBN (0.000548 mol; 0.100 mL of stock 0.0248-mmol solution made by dissolving 4.50 mg AIBN in 10 mL THF; 0.000137 equiv), and 3 mL THF. The clear, colorless solution was heated to reflux for 24 h–36 h, at which point most of the solvent had evaporated and the reaction contained a light yellow solid. This polymeric material is insoluble in THF, and forms a gel-like substance in a mixture of THF-DMF.

Incorporation of pentylhydroxy AB. After washing to remove any traces of the initiator, the polymer is suspended in THF and DMF (1:1; 2 mL each), and charged with TEA (0.300 ml; 2.14 mmol; 2.14 equiv compared to the number of carboxylates present), DMAP (8.00 mg; 0.0655 mmol; 0.033 equiv), EDAC (9.10 mg; 0.0475 mmol; 0.024 equiv) and pentyl hydroxy AB (8.70 mg; 0.0204 mmol; 0.0102 equiv). The reaction is heated at 80° C. under a positive pressure of nitrogen. The reaction mixture is a white opaque gel-like solid, and the reaction is monitored by following incorporation of AB via long wavelength UW light. After 24 h, the reaction mixture is cooled to room temperature, and poured into 100 ml-water. The solid gel-like material is washed with water (30×10 mL) and finally soaked in 100 ml. water for 24 h to remove any leachables.

Carboxypolystyrene with Higher Pentylhydroxy AB Content

One advantage of the disclosed methods is the generation of Carboxy polystyrene with higher pentylhydroxy AB content as illustrated in FIG. 8 (but with a ~5–10% AB content). The advantage of attaching fluorophores to premade designed polymers is that the amount of fluorophore can be varied quite easily. This has advantages since fluorescence output often depends on concentration of fluorophore and if it is necessary to vary amount of fluorophore for this reason or any other, then it is quite easy to carry out. The rational basis for this particular experiment came about when solution studies demonstrated that higher AB content gives higher transductions. The method of preparation is similar to that of the ca. 1% AB attached carboxypolystyrene.

Example 3

Standard Method of Obtaining Transductions in Films

Films ate either stuffed in a quartz microcuvette with a 0.75 mL capacity, or fixed between a pair of half opened paper clips or in a mesh (simply used to hold the film steady and uptight) in a disposable polyacrylate cuvette. After obtaining a steady baseline (important for films), glucose is added as a "spike" usually of 0.100 mL of stock 5000 mg/dL stock solution. This gives a final ca 125 mg/dL-165 mg/dL glucose concentration depending on the volume of solution in the disposable cuvette. It is slightly mote challenging to determine the amount of glucose in the quartz microcuvette since the volumes ate more difficult to measure and the additions are more difficult to make. For example, an addition of 0.050 mL of 5000 mg/dL gives a 333 mg/dL glucose spike assuming a total volume of 0.75 mL. The total volume is difficult to estimate since the film occupies some of the space as well. In almost all cases at present, the mesh method is used to hold the film in the disposable polyacrylate cuvette.

Figure 18:
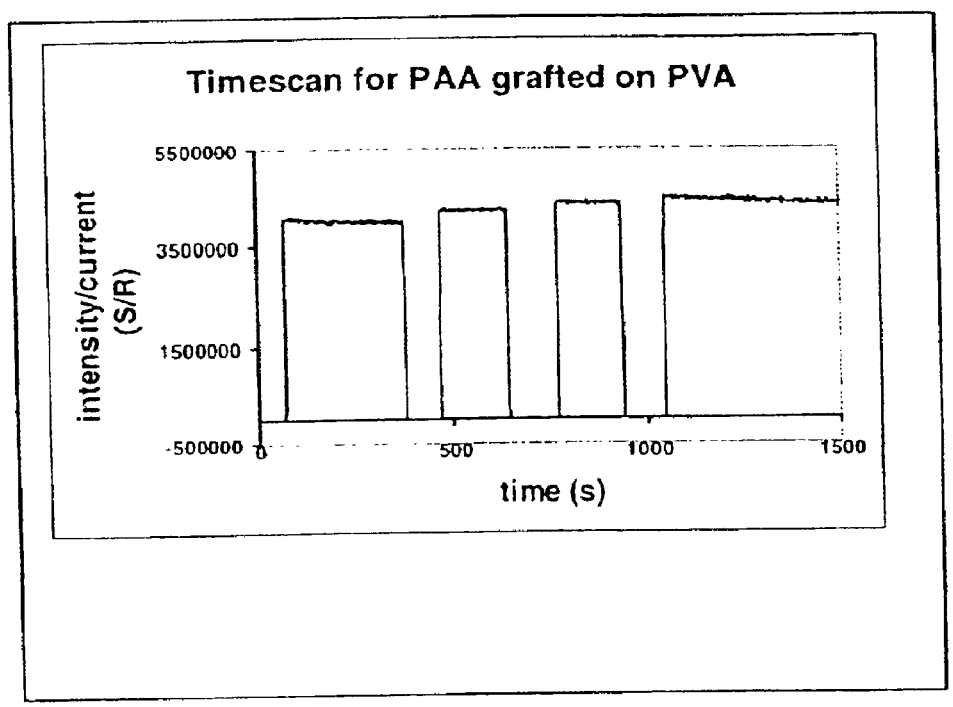
FIG. 18 provides the results of a timescan showing glucose transduction with a polymer made by grafting a fluorophore and polyacrylic acid (PAA) onto polyvinylalcohol (PVA).

All of the film transductions are carried out in a similar manner at present. In case of polymer films, front face analysis is used to obtain lower scattering of light. Time scan spectra are obtained either in the S or the S/R mode depending on the sensitivity required. Slit widths, and excitation and emission maxima are experimentally determined. Glucose additions are made after disconnecting the phototnultiplier tube (PMT), and results in what appears as a drop in the reading in an apparent square wave manner with the intensity readings dropping to zero. Reconnecting the PMT shows either unchanged fluorescence or an increase indicating optical amplification as a result of signal transduction when the glucose interacts with the boronate entity. Such changes are followed and plotted to reveal the changes that occur in the optical signal with increasing amounts of glucose. In the timescan in FIG. 18, a grafted polyacrylic acid-polyvinyl alcohol polymer with an attached fluorophore is shown to signal transduction with increasing glucose aliquots.

Figure 15:
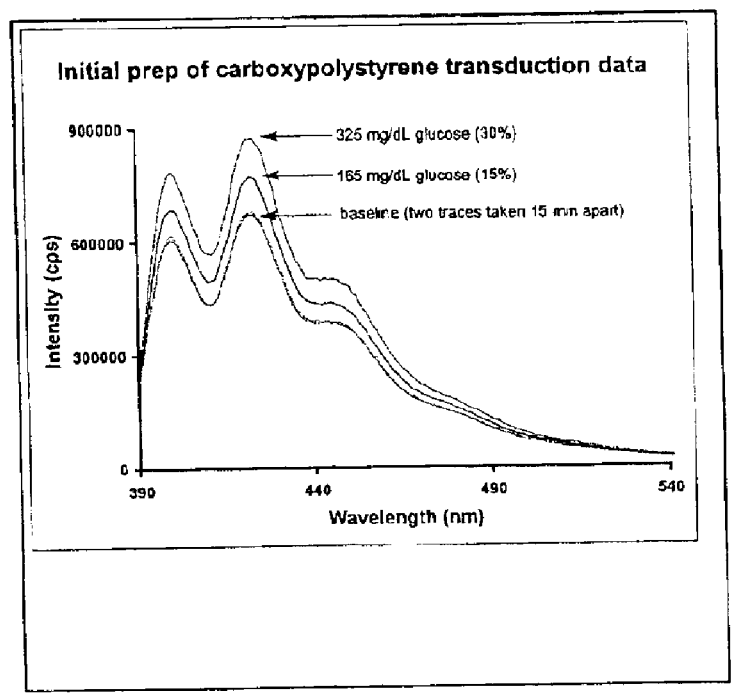
FIG. 15 provides data from transductions obtained with glucose of the carboxypolystyrene modified with ca. 1% AB.

In the cases where normal intensity spectra are obtained, sampling is done over a range of wavelengths to sufficiently cover the entire emission spectrum. Aliquots of glucose are added and spectra are recorded and then compared for transduction, which is revealed by increases in intensity of the fluorescence output, as seen in FIG. 15. The experiment has been reproduced with the same piece of film and just as a comparison to the solution phase data (using DMSO as spike solvent), the transduction obtained at ca. 200 mg/dL glucose using the higher concentration pentylhydroxy AB attached to carboxypolystyrene is ca. 35%–40%. This is approximately one-half of that in solution, where pentylhydroxy AB in aq. PBS gives ca. 80% transduction at ca. 200 mg/dL glucose.

Example 4

Implant/Explant Techniques for Evaluating Sensor Embodiments

Rats can be used in order to evaluate different methods for placing the sensor. The sensor can be designed to be unobtrusive for implant. A small bead fits this criterion and may be placed easily under the skin. Implantation can involve a small incision or the use of a trocar. Explanting of sensors can be conducted at various time intervals along the course of the studies. As such, several experiments can be conducted utilizing different explant techniques, e.g., removal of fibrous capsule surrounding implant vs. not removing capsule.

Detailed Kinetics & In Vitro Longevity

12 Week In Vitro Longevity (PBS @ 37° C.)

The sensor (implant) is positioned at the center of a fluorescence cuvet containing degassed PBS, the spectrometer is configured to monitor at the emission wavelength ($\lambda_{em}$) of the fluorescent boronic acid (FBA), and the fluorescence signal is recorded in the time-scan mode. After achieving a constant baseline, the cuvet is spiked with a glucose standar in order to raise the glucose concentration to 200 mg/dL. From the time scan, the percent transduction is calculated and recorded. The study samples are allowed to remain in 200 mg/dL glucose for an additional hour at which time they are removed, rinsed and placed into PBS, until the next scheduled reading. This experiment is repeated daily for a period of twelve weeks for each sensor in the test population, and the data are compared as a means of evaluating performance over time.

In a separate experiment, sensors are exposed to a constant glucose concentration of 150 mg/dL in PBS. These samples are to be used to evaluate the signal intensity (reproducibility) as a function of time whereby the fluorescence intensity can be measured daily for the duration of the 12-week experiment. Based upon the results with poly (carboxy-styrene)-FBA sensing polymer, deterioration in the fluorescence signal is not anticipated. These evaluations can yield important information about the sensitivity, rate at which the sensor responds, and in vitro lifetime and reproducibility of the sensor. All samples can be compared within respective groups as well as v. external control samples evaluated over the 12-week period. All samples are stored at 37° C. in an incubator between readings, all solvents are degassed prior to use and cuvets are to be sealed and stored in the dark in order to minimize effects of photobleaching of the fluorophore.

Example 5

12 week In Vitro Longevity (Human Plasma @37° C.)Techniques for Evaluating Sensor Embodiments The identical experiments to those detailed in the above section can be carried out in reconstituted human plasma (Sigma Chemical) treated with antibiotic-antimycotic (100×, 10 µl/ml). Because the shelf life of the test plasma must be carefully considered, the plasma can be spiked with antibiotic-antimycotic every 3–4 days and exchanged for new plasma every two weeks. The data from these studies can be evaluated in the protocols disclosed herein.

In Vitro Kinetics

Each polymer (matrix & fluorophote concentration), kinetic studies in a temperature-controlled flow cell (Starna) can be performed. Continuous measurements of the sensor response can be made as the concentration of glucose is altered in the flow cell. Because boronate-saccharide molecular recognition events are extremely fast ($10^{8-10}$ $M^{-1}s^{-1}$) in the studies conducted on poly(4-carboxy styrene), and other materials (i.e. on the order of seconds), in general, one can expect that the kinetics of these systems are extremely fast. Furthermore, given that interstitial glucose lags blood glucose by approximately 10 minutes, the time constant of the sensor is expected to be a minor contributor to any time delay for this optochemical sensor (See, e.g. Rebrin et al.,. Am.J.Physiol. 1999, 277, E561–E571). Thus these studies are to be performed in order to be comprehensive in the characterization of the sensor. For these studies, the timescan profile provides the important details about the kinetics with the time constant easily calculated by integrating the fluorescence signal data over the two steady-state concentration regions of interest, e.g. $SS_{g0}$ (glucose=0 mg/dL) and $SS_{g100}$ (glucose=100 mg/dL).

The glucose concentrations are chosen to encompass the (human) physiological range. In the first flow cell experiment of set, 0⇌50, the sample is mounted into the flow cell and the baseline is stabilized using $PBS_0$ pumped at a flow rate of 5 ml/minute. Next, 50 mg/dL glucose in PBS ($PBS_{50}$) is pumped into the cell and the fluorescence emission ($\lambda_{em}$) measured as a function of time (time scan mode, SPEX FluoroLog). At each concentration, the sample is allowed to dwell for an additional 10 minutes prior to changing the glucose concentration. After the dwell at $PBS_0$, $PBS_{100}$ is pumped into the system and the time scan recorded.

Following the collection of the data for each experiment, the half-time ($t_{1/2}$) can be calculated for each of the above reactions (rising & falling). The half-time is defined as the time to reach the 1/2 point of the equilibrium. A plot of $t_{1/2}$ versus the change in glucose concentration for each experiment, when compared to a plot of $t_{1/2}$ versus starting glucose concentration can provide insight into whether the kinetics are dependent upon the starting glucose concentration or the change in glucose concentration at each point. These experiments are designed to enable us to better understand the kinetics of the sensor under conditions designed to mimic those that may be observed in vivo.

In Vitro Kinetics (Human Plasma)

The identical experiments to those detailed in the above section can be carried out in reconstituted human plasma (Sigma Chemical) treated with antibiotic-antimycotic (100×,10 µl/ml) in order to evaluate the kinetics in the presence of protein and to determine if fouling of the surface may affect the sensor time constant. Because the shelf life of the test plasma must be carefully considered, the plasma can be spiked with antibiotic-antimycotic every 3–4 days and exchanged for new plasma every two weeks. The data from these studies can be evaluated in the same fashion as in the previous section.

Example 6

Flow-cell Experiments Testing Reversibility of Glucose Sensor

Sensor kinetics can be conducted using sensors that have been optimized according to the methods provided herein. These studies can be conducted in the hyperglycemic and hypoglycemic rat models described herein.

Functionality testing of the improved sensors can be carried out as described herein. Sensor functionality measurements are conducted post implantation and at 4 week intervals thereafter. These studies can focus on long-term functionality of the sensor. One can evaluate and compare data sets over time in order to provide insight to the sensor sensitivity/signal intensity.

The operation of the sensor needs to be evaluated as a function of animal model, implantation depth, implant technique, and skin pigment. In order to evaluate all of these variables, three animal models can be utilized (rat, dog, pig). The use of three species allows us to evaluate the interspecies variability as well as variations within the same model depending upon implant depth, method etc. Furthermore, the ability of the sensor to perform over time longevity) can be evaluated in large animals (dog, pig).

All samples are removed from the animal at an indicated time point and the tissue is fixed in formalin and analyzed using standard histopathology. The explanted sensor is evaluated for glucose response, analyzed using SEM to look for material degradation and other anomalies, and chemically analyzed (GPC, FTIR, elemental analysis) in order to characterize the material following exposure in vivo. These parameters enable us to understand some of the variability anticipated in a clinical setting including effects of surgical technique and population diversity.

Example 8

In Vivo Studies

Figure 19A:
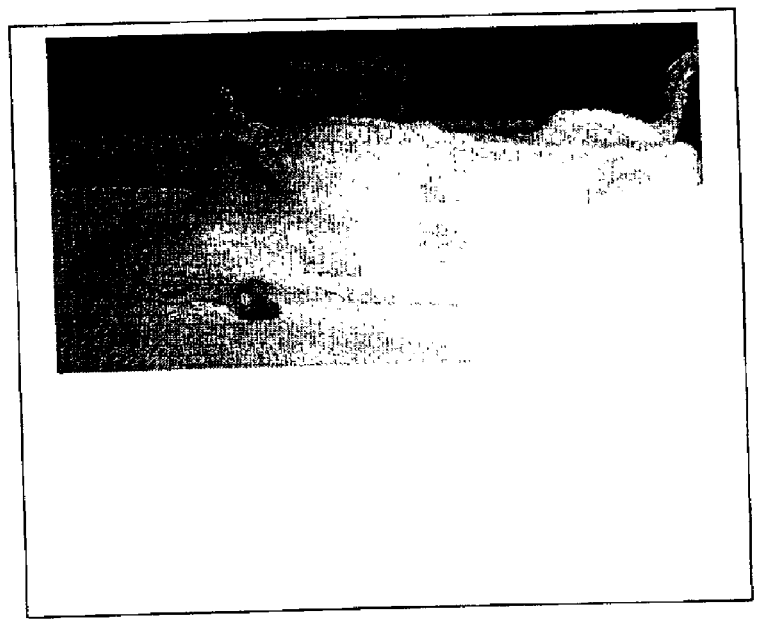
FIG. 19A shows an anesthetized rodent with a prototype glucose sensor (Embedded in Ear) consisting of AB in pHEMA. Short wavelength light is shined from the dorsal side, resulting in the sensor to "light up" the ear via emission at a longer wavelength.

For illustrative in vivo studies, AB was covalently tethered to pHEMA hydrogel providing a biocompatible matrix that offered excellent glucose permeability. After casting the polymer into a thin film configuration, the polymer was implanted into the ear of a rat and interrogated using a fiberoptic to collect light and direct it into the emission monochrometer of a spectrofluorometer (Photon Technology International, South Brunswick, N.J.). FIG. 19A. shows a rat with a sensor implanted in its ear and a green emission at the center of the excitation source.

Figure 19B:
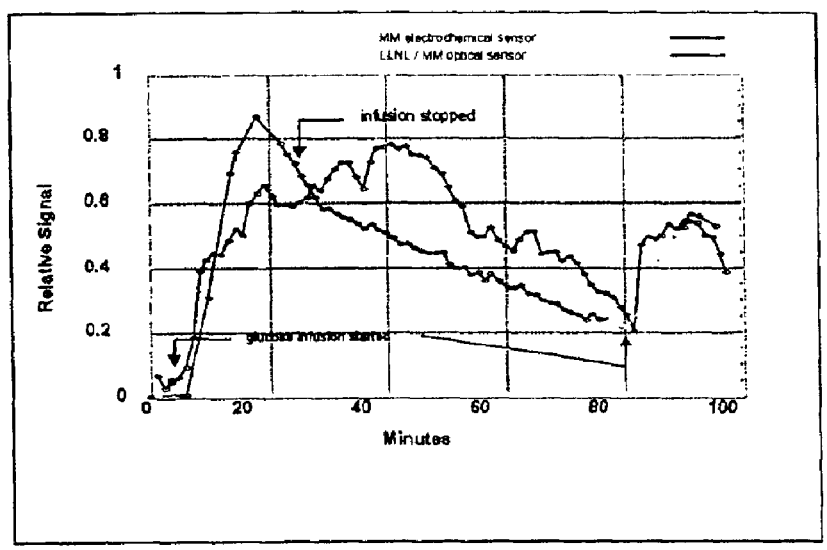
FIG. 19B provides a comparison of electrochemical and optical sensor via clamp study in a rodent.
Figure 20A:
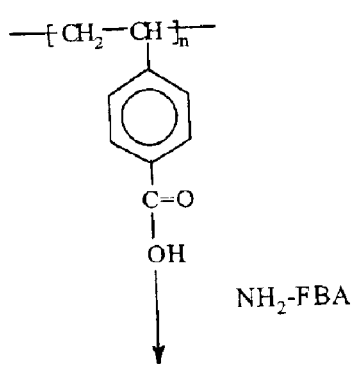
FIGS. 20A–20I provide schematic representations of various fluorescent boronic acid (FBA) species that can be attached to polymers (in this figure as illustrated by functionalized polystyrenes) through a variety of covalent grafting protocols known in the art (e.g. using transformation reagents such as dicyclohexylcabodiirnide, $PCl_5$, $COCl_2$, $SOCl_2$ etc.). See also Table 2.
Figure 20A:
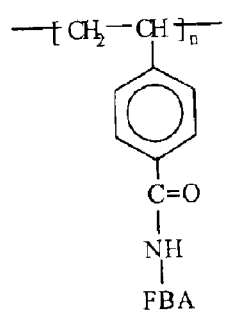
Figure 20B:
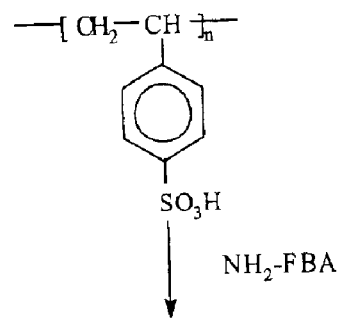
Figure 20B:
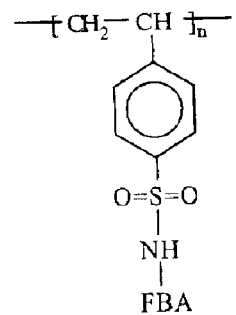
Figure 20C:
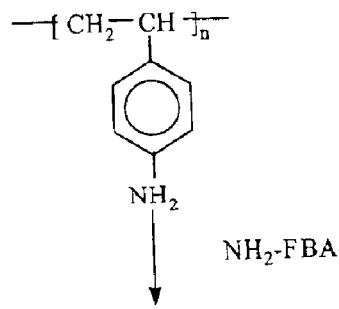
Figure 20C:
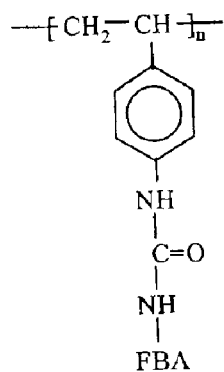
Figure 20D:
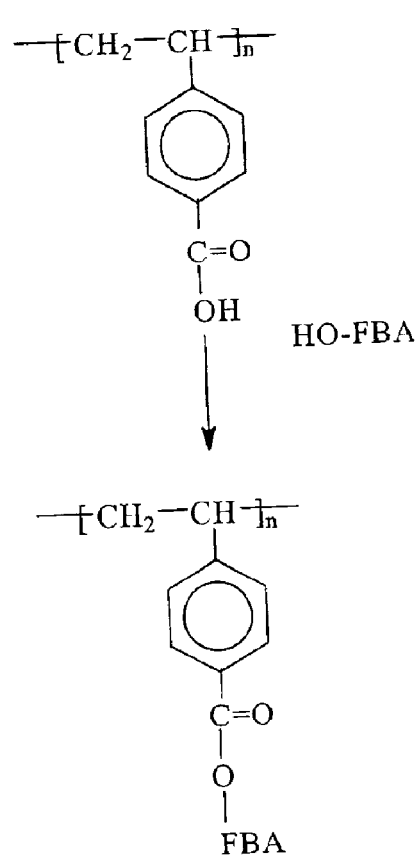
Figure 20E:
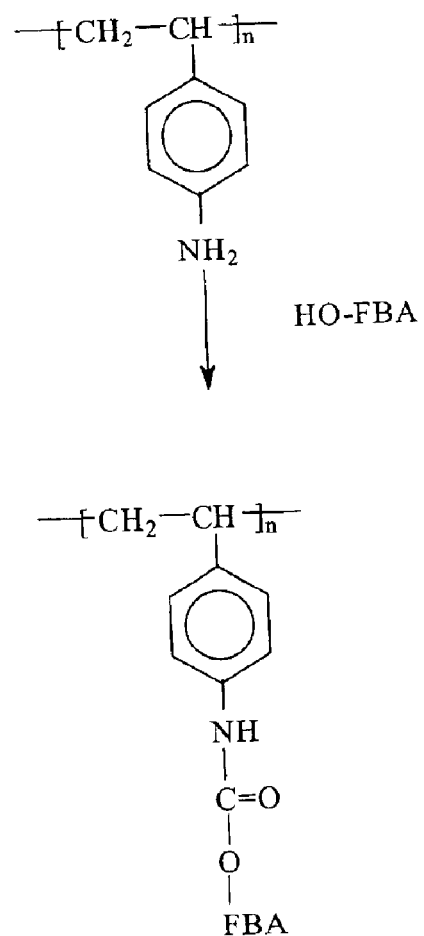
Figure 20F:
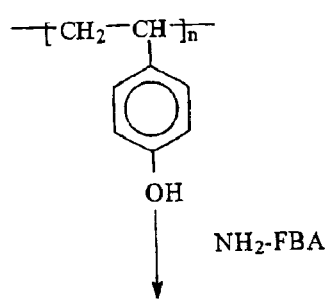
Figure 20F:
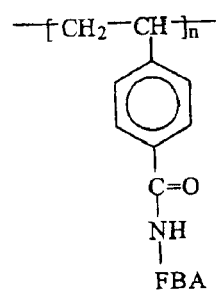
Figure 20G:
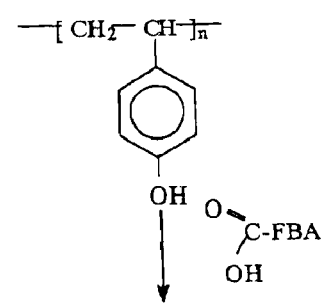
Figure 20G:
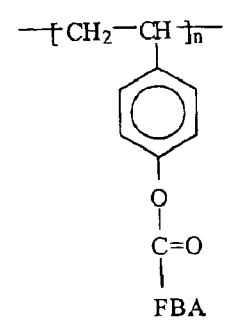
Figure 20H:
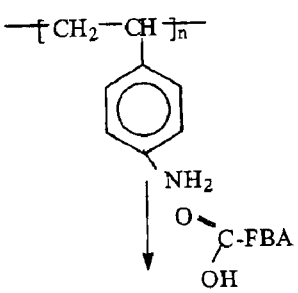
Figure 20H:
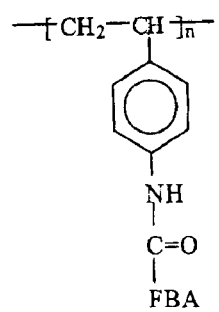
Figure 20I:
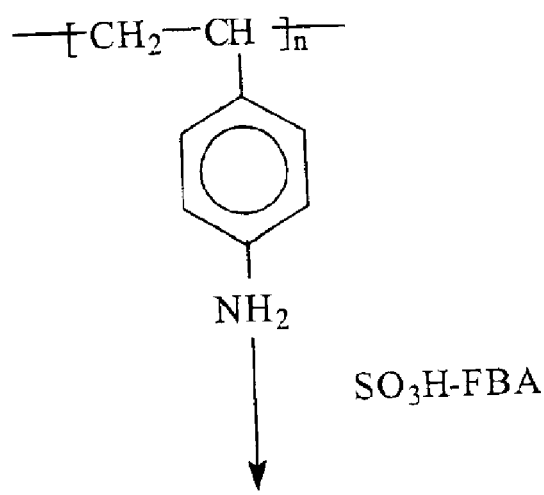
Figure 20I:
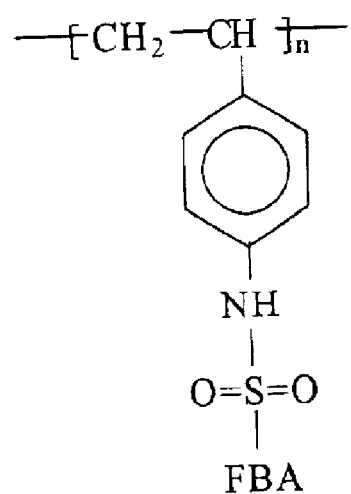

Following the implantation of the sensor material, the rat was administered a hyperglycemic clamp by continuous controlled glucose infusion and the response of the sensor plotted as a function of time. An electroenzymatic glucose sensor provided a control glucose profile as detailed in FIG. 19B.

Example 9

Biologic Interactions with Sensors and Sensor Materials

For studies of biosensor membranes, films, and chamber-type sensor probes, one can investigate the biocompatibility of silicon nitride, non-functioning chamber-type, silicon-based sensor probes, Nafion membranes, Nafion coated polyethylene and a series of plasma polymerized films on polyethylene using the cage implant system (see, e.g. Kao W J and Anderson J M). The cage implant system: In vivo evaluation of inflammatory responses to biomaterials, in Handbook of Biomaterials Evaluation, 2nd edition, Chapter 42, von Recum A F, Ed, Taylor and Francis, 1998, pp 649–659Marchant R, Hiltner A, Hamlin C, Rabinovitch A, Slobodkin R and Anderson J M. In vivo biocompatibility studies: I. The cage implant system and a biodegradable hydrogel, J Biomed Mater Res 1983; 17:301–325; and Marchant R E, Phua K, Hiltner A, and Anderson J M. In tivo biocompatibility studies: II. Biomer®: Preliminary cell adhesion and surface characterization studies, J Biomed Mater Res 1984; 18:309–315) Biocompatibility studies on silicon nitride were performed using four groups of glass samples coated on one side with silicon nitride, each having been prepared by a different combination of methods of vapor deposition and heat treatment. The results from the analysis of inflammatory exudates indicate the silicon nitride coatings do not induce an adverse inflammatory response compared with empty-cage control implants. The biological response to non-finctioning, chamber-type probes was evaluated using the in tivo cage implant system.

Throughout the specification various patents, patent applications and other publications are referenced. The entire content of these patents, patent applications and other publications ate incorporated herein by reference.

What is claimed is:

1. A polymer composition comprising a fluorescent boronic acid of the general formula:

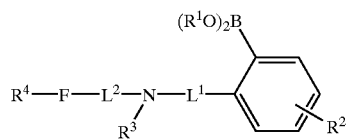

wherein:
F is a fluorophore;
N is a nitrogen atom;
B is a boron atom;
$R^1$ is selected from the functional group consisting of hydrogen, aliphatic and aromatic groups, wherein the functional group $(R^1O)_2B$ is capable of binding glucose;
$R^2$, $R^3$ and $R^4$ are optional and independent hydrogen, aliphatic or aromatic groups, further functionalized aliphatic or aromatic groups or groups that are capable of forming a covalent linkage to the polymer matrix, wherein the polymerized matrix is a polystyrene or a polyvinylalcohol;
$L^1$ and $L^2$ ate optional linking groups having from zero to four atoms selected from the group consisting of nitrogen, carbon, oxygen, sulfur and phosphorous; and
wherein the polymer composition futher includes a reference fluorophore; and wherein the fluorescent boronic acid and the reference fluorophore are covalently coupled to the polymer matrix after polymerization; and
further wherein:
the polymer composition including the covalently coupled reference fluorophore and the covalently coupled fluorescent boronic acid is soluble in an aqueous environment; and
the fluorescence of the polymer composition including the covalently coupled reference fluorophore and the covalently coupled fluorescent boronic acid increases in the presence of bound glucose.

2. The polymer composition of claim 1, wherein the polymer composition further includes an additional polymer that is coupled to the polymer matrix after polymerization; and wherein the additional polymer enhances the biocompatibility, swellability or hydrophllicity of the polymer composition.

3. The polymer composition of claim 2, wherein the polymer matrix is a block copolymer.

4. The polymer composition of claim 2, wherein the additional polymer is grafted on to the polymer matrix.

5. The polymer composition of claim 2, wherein the additional polymer is a polyethyleneoxide or polyethyleneoxide-polypropyleneoxide compound.

6. The polymer composition of claim 2, wherein the polymer matrix is crosslinked.

7. The polymer composition of claim 6, wherein the polymer matrix is crosslinked with polyethyleneoxide or polyethyleneoxide-polypropyleneoxide compounds.

8. The polymer composition of claim 1, wherein the nitrogen atom in the fluorescent boronic acid is covalently coupled to the polymer matrix after polymerization via the group designated $R^3$.

9. The polymer composition of claim 8, wherein the atoms that link the fluorescent boronic acid to the polymer matrix of the polymer composition enhance the solubility of the polymer composition.

10. The polymer composition of claim 1, wherein the polymerized matrix is a polystyrene.

11. The polymer composition of claim 10, wherein the tether that links the polymer matrix (PM) to the fluorescent boronic acid (FBA) includes the following atoms: PM-CO-NH—FBA; PM-SO$_2$—NH—FBA; PM-CO—NH—FBA; PM-COO—FBA; PM-NH—COO—FBA; PM-NH—CO—N—FBA or PM-NH—SO$_2$—FBA, wherein C denotes carbon, N denotes nitrogen, O denotes oxygen, S denotes sulfur and H denotes hydrogen.

12. The polymer composition of claim 1, wherein the fluorophore is highly soluble in water.

13. The polymer composition of claim 12, wherein the fluorophore is Nile Blue.

14. A polymer composition comprising a fluorescent boronic acid and a reference fluorophore; wherein the composition is produced by a process of covalently coupling the fluorescent boronic acid and the reference fluorophore to a polymerized matrix, wherein the fluorescent boronic acid has the general formula:

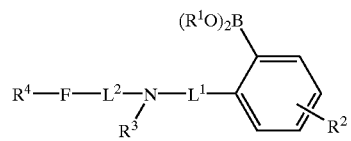

wherein:
F is a fluorophore;
N is a nitrogen atom;
B is a boron atom;
$R^1$ is selected from the functional group consisting of hydrogen, aliphatic and aromatic groups, wherein the functional group $(R^1O)_2B$ is capable of binding glucose;
$R^2$, $R^3$ and $R^4$ are optional and independent hydrogen, aliphatic or aromatic groups, further functionalized aliphatic or aromatic groups or groups that are capable of forming a covalent linkage to the polymer matrix, wherein the polymerized matrix is a polystyrene or a polyvinylalcohol;

L¹ and L² ate optional linking groups having from zero to four atoms selected from the group consisting of nitrogen, carbon, oxygen, sulfur and phosphorous; and wherein the polymer composition including the covalently coupled reference fluorophore and the covalently coupled fluorescent boronic acid is soluble in an aqueous environment; and the fluorescence of the polymer composition including the covalendy coupled reference fluorophore and the covalently coupled fluorescent boronic acid increases in the presence of bound glucose.

15. The polymer composition of claim 14, wherein the polymer composition further includes an additional polymer that is covalently coupled to the polymerized matrix; and wherein the additional polymer enhances the solubility of the polymer composition.

16. The polymer composition of claim 15, wherein the polymerized matrix is a block copolymer.

17. The polymer composition of claim 15, wherein the additional polymer is grafted on to the polymerized matrix.

18. The polymer composition of claim 15, wherein the additional polymer is a polyethyleneoxide or polyethyleneoxide-polypropyleneoxide compound.

19. The polymer composition of claim 15, wherein the polymerized matrix is crosslinked.

20. The polymer composition of claim 19, wherein the polymerized matrix is crosslinked with polyethyleneoxide or polyethyleneoxide-polypropyleneoxide compounds.

21. The polymer composition of claim 14, wherein the nitrogen atom in the fluorescent boronic acid is covalently coupled to the polymerized matrix via the group designated $R^3$.

22. The polymer composition of claim 21, wherein the atoms that link the fluorescent boronic acid to the polymerized matrix of polymer composition enhance the solubility of the polymer composition.

23. The polymer composition of claim 14, wherein the polymerized matrix is a polystyrene.

24. The polymer composition of claim 23, wherein the tether that links the polymer matrix (PM) to the fluorescent boronic acid (FBA) includes the following atoms: PM-CO—NH—FBA; PM-SO$_2$—NH—FBA; PM-CO—NH—FBA; PM-COO—FBA; PM-NH—COO—FBA; PM-NH—CO—N—FBA or PM-NH—SO$_2$—FBA, wherein C denotes carbon, N denotes nitrogen, O denotes oxygen, S denotes sulfur and H denotes hydrogen.

25. The polymer composition of claim 14, wherein the fluorophore is highly soluble in water.

26. The polymer composition of claim 25, wherein the fluorophore is Nile Blue.

* * * * *